(12) United States Patent
Chen et al.

(10) Patent No.: US 8,501,182 B2
(45) Date of Patent: Aug. 6, 2013

(54) **MONOCLONAL ANTIBODIES THAT REACT WITH THE CAPSULE OF *BACILLUS ANTHRACIS***

(75) Inventors: Zhaochun Chen, North Potomac, MD (US); Robert H. Purcell, Gaithersburg, MD (US); Rachel Schneerson, Bethesda, MD (US); Joanna Kubler-Kielb, Bethesda, MD (US); Lily Z. Dai, Deerwood, MD (US)

(73) Assignee: The United States of America, as Represented by the Secretary of the Department of Health and Human Services, Washington, DC (US)

( * ) Notice: Subject to any disclaimer, the term of this patent is extended or adjusted under 35 U.S.C. 154(b) by 110 days.

(21) Appl. No.: 13/130,044

(22) PCT Filed: Nov. 19, 2009

(86) PCT No.: PCT/US2009/065198
§ 371 (c)(1),
(2), (4) Date: May 18, 2011

(87) PCT Pub. No.: WO2010/077473
PCT Pub. Date: Jul. 8, 2010

(65) Prior Publication Data
US 2011/0223163 A1  Sep. 15, 2011

Related U.S. Application Data

(60) Provisional application No. 61/116,222, filed on Nov. 19, 2008.

(51) Int. Cl.
*A61K 39/40* (2006.01)
(52) U.S. Cl.
USPC .................. 424/150.1; 424/130.1; 424/133.1; 424/164.1; 530/300; 530/387.1; 530/387.3; 530/388.4; 435/7.32; 435/320.1; 435/325; 435/340

(58) Field of Classification Search
USPC ..... 530/300, 387.1, 387.3, 388.4; 424/130.1, 424/133.1, 150.1, 164.1; 435/7.32, 320.1, 435/325, 340
See application file for complete search history.

(56) References Cited

FOREIGN PATENT DOCUMENTS
WO  WO 2005/000884  1/2005

OTHER PUBLICATIONS

Kozel et al., "mAbs to *Bacillus anthracis* capsular antigen for immunoprotection in anthrax detection of antigenemia," *PNAS*, 101(14): 5042-5047, 2004.
Kozel et al., "Protective and Immunochemical Activities of Monoclonal Antibodies Reactive with the *Bacillus anthracis* Polypeptide Capsule," *Infection and Immunity*, 75(1): 152-163, 2007.
Kubler-Kielb et al., "Additional conjugation methods and immunogenicity of *Bacillus anthracis* poly-γ-D-glutamic acid-protein conjugates," *Infection and Immunity*, 74(8): 4744-4749, 2006.
Schneerson et al., "Poly(γ-D-glutamic acid) protein conjugates induce IgG antibodies in mice to the capsule of *Bacillus anthracis*: A potential addition to the anthrax vaccine," *PNAS*, 100(15): 8945-8950, 2003.

*Primary Examiner* — Stephen Rawlings
(74) *Attorney, Agent, or Firm* — Klarquist Sparkman, LLP

(57) ABSTRACT

The present disclosure relates to monoclonal antibodies that bind poly-γ-D-glutamic acid (γDPGA), which is present on the surface of *Bacillus anthracis*. The disclosure also provides chimeric forms of the monoclonal antibodies, humanized forms of the monoclonal antibodies, and fragments thereof, as well as nucleic acids encoding the antibodies and fragments thereof. Pharmaceutical compositions including such antibodies are also disclosed herein. The disclosure further provides prophylactic, therapeutic, and diagnostic methods of using the disclosed antibodies.

29 Claims, 5 Drawing Sheets

FIG. 1A

```
         Framework 1                 CDR1    Framework 2        CDR 2
4C   LEESGGGLVKPGDSLRLSCAASGFTFS    VYAMH   WVRQAPEKGLEWVS    TIGAGGNTW
11D  ..........G.T........-.....    ....T   ..............    ...RS.D.L Framework 3                         CDR 3
4C   HSDSVKGRYTIARDNSQNTLSLQMNSLRAEDTAVYYCVR   RGYCSSTRCDSNDAFDI
11D  Y......FS.S....K..Y.............A......   K.......N.Q.QYY..Y Framework 4
4C   WGQGTMVTVS
11D  ......L...
```

FIG. 1B

```
         Framework 1                 CDR 1           Framework 2        CDR 2
4C   APMTQSPSSLSASVGDRVSITC        RASQDINDFLA      WFQQKPGKAPKRLI    FRTSSLQG
11D  -EL..................         .....V.TW..      .....Y......P.    YAA.....

Framework 3                  CDR 3          Framework 4
4C   GVSSRFSGSGSGTEFTLTISNLRPEDFATYYC   LQHSSYPPT    FGQGTKLEISRT
11D  ..P..............D......S.Q.....   Q.YKH..L.    ...G...V..K.
```

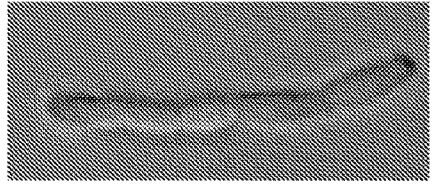
FIG. 3A
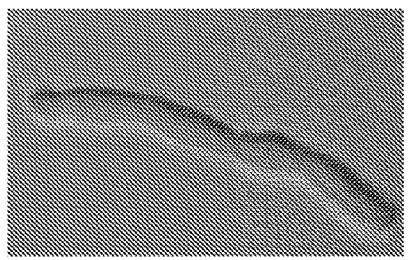
FIG. 3B
Anti-PA W1 IgG 100 µg/ml
FIG. 3E
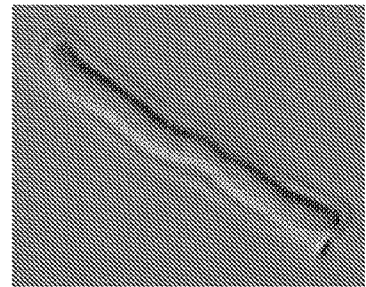
FIG. 3D
Anti-PGA Fab, 100 µg/ml
FIG. 3C
Anti-PGA IgG:   25 µg/ml   50 µg/ml   100 µg/ml

SEQUENCE LISTING

```
<160> NUMBER OF SEQ ID NOS: 18

<210> SEQ ID NO 1
<211> LENGTH: 121
<212> TYPE: PRT
<213> ORGANISM: Artificial sequence
<220> FEATURE:
<223> OTHER INFORMATION: Consensus anti-gamma DPGA antibody heavy chain
      variable domain sequence
<220> FEATURE:
<221> NAME/KEY: VARIANT
<222> LOCATION: (3)..(3)
<223> OTHER INFORMATION: X1 can be E or no amino acid
<220> FEATURE:
```

```
<221> NAME/KEY: VARIANT
<222> LOCATION: (13)..(13)
<223> OTHER INFORMATION: X2 can be D or G
<220> FEATURE:
<221> NAME/KEY: VARIANT
<222> LOCATION: (16)..(16)
<223> OTHER INFORMATION: X3 can be R or T
<220> FEATURE:
<221> NAME/KEY: VARIANT
<222> LOCATION: (28)..(28)
<223> OTHER INFORMATION: X4 can be V or T
<220> FEATURE:
<221> NAME/KEY: VARIANT
<222> LOCATION: (50)..(50)
<223> OTHER INFORMATION: X5 can be A or R
<220> FEATURE:
<221> NAME/KEY: VARIANT
<222> LOCATION: (51)..(51)
<223> OTHER INFORMATION: X6 can be G or S
<220> FEATURE:
<221> NAME/KEY: VARIANT
<222> LOCATION: (53)..(53)
<223> OTHER INFORMATION: X7 can be N or D
<220> FEATURE:
<221> NAME/KEY: VARIANT
<222> LOCATION: (55)..(55)
<223> OTHER INFORMATION: X8 can be W or L
<220> FEATURE:
<221> NAME/KEY: VARIANT
<222> LOCATION: (56)..(56)
<223> OTHER INFORMATION: X9 can be H or Y
<220> FEATURE:
<221> NAME/KEY: VARIANT
<222> LOCATION: (64)..(64)
<223> OTHER INFORMATION: X10 can be Y or F
<220> FEATURE:
<221> NAME/KEY: VARIANT
<222> LOCATION: (65)..(65)
<223> OTHER INFORMATION: X11 can be T or S
<220> FEATURE:
<221> NAME/KEY: VARIANT
<222> LOCATION: (67)..(67)
<223> OTHER INFORMATION: X12 can be A or S
<220> FEATURE:
<221> NAME/KEY: VARIANT
<222> LOCATION: (72)..(72)
<223> OTHER INFORMATION: X13 can be Q or K
<220> FEATURE:
<221> NAME/KEY: VARIANT
<222> LOCATION: (76)..(76)
<223> OTHER INFORMATION: X14 can be S or Y
<220> FEATURE:
<221> NAME/KEY: VARIANT
<222> LOCATION: (93)..(93)
<223> OTHER INFORMATION: X15 can be V or A
<220> FEATURE:
<221> NAME/KEY: VARIANT
<222> LOCATION: (95)..(95)
<223> OTHER INFORMATION: X16 can be R or K
<220> FEATURE:
<221> NAME/KEY: VARIANT
<222> LOCATION: (102)..(102)
<223> OTHER INFORMATION: X17 can be R or N
<220> FEATURE:
<221> NAME/KEY: VARIANT
<222> LOCATION: (104)..(104)
<223> OTHER INFORMATION: X18 can be D or Q
<220> FEATURE:
<221> NAME/KEY: VARIANT
<222> LOCATION: (106)..(106)
<223> OTHER INFORMATION: X19 can be N or Q
<220> FEATURE:
<221> NAME/KEY: VARIANT
<222> LOCATION: (107)..(107)
<223> OTHER INFORMATION: X20 can be D or Y
<220> FEATURE:
<221> NAME/KEY: VARIANT
<222> LOCATION: (108)..(108)
<223> OTHER INFORMATION: X21 can be A or Y
<220> FEATURE:
```

```
<221> NAME/KEY: VARIANT
<222> LOCATION: (111)..(111)
<223> OTHER INFORMATION: X22 can be I or Y
<220> FEATURE:
<221> NAME/KEY: VARIANT
<222> LOCATION: (117)..(117)
<223> OTHER INFORMATION: X23 can be M or L

<400> SEQUENCE: 1

Leu Glu Xaa Ser Gly Gly Gly Leu Val Lys Pro Gly Xaa Ser Leu Xaa
1               5                   10                  15

Leu Ser Cys Ala Ala Ser Gly Phe Thr Phe Ser Xaa Tyr Ala Met His
            20                  25                  30

Trp Val Arg Gln Ala Pro Glu Lys Gly Leu Glu Trp Val Ser Thr Ile
        35                  40                  45

Gly Xaa Xaa Gly Xaa Thr Xaa Xaa Ser Asp Ser Val Lys Gly Arg Xaa
    50                  55                  60

Xaa Ile Xaa Arg Asp Asn Ser Xaa Asn Thr Leu Xaa Leu Gln Met Asn
65              70                  75                  80

Ser Leu Arg Ala Glu Asp Thr Ala Val Tyr Tyr Cys Xaa Arg Xaa Gly
                85                  90                  95

Tyr Cys Ser Ser Thr Xaa Cys Xaa Ser Xaa Xaa Xaa Phe Asp Xaa Trp
            100                 105                 110

Gly Gln Gly Thr Xaa Val Thr Val Ser
            115                 120

<210> SEQ ID NO 2
<211> LENGTH: 108
<212> TYPE: PRT
<213> ORGANISM: Artificial sequence
<220> FEATURE:
<223> OTHER INFORMATION: Consensus anti-gamma DPGA antibody light chain
      variable domain sequence
<220> FEATURE:
<221> NAME/KEY: VARIANT
<222> LOCATION: (1)..(1)
<223> OTHER INFORMATION: X1 can be A or no amino acid
<220> FEATURE:
<221> NAME/KEY: VARIANT
<222> LOCATION: (2)..(2)
<223> OTHER INFORMATION: X2 can be P or E
<220> FEATURE:
<221> NAME/KEY: VARIANT
<222> LOCATION: (3)..(3)
<223> OTHER INFORMATION: X3 can be M or L
<220> FEATURE:
<221> NAME/KEY: VARIANT
<222> LOCATION: (16)..(16)
<223> OTHER INFORMATION: X4 can be D or G
<220> FEATURE:
<221> NAME/KEY: VARIANT
<222> LOCATION: (19)..(19)
<223> OTHER INFORMATION: X5 can be S or T
<220> FEATURE:
<221> NAME/KEY: VARIANT
<222> LOCATION: (28)..(28)
<223> OTHER INFORMATION: X6 can be I or V
<220> FEATURE:
<221> NAME/KEY: VARIANT
<222> LOCATION: (30)..(30)
<223> OTHER INFORMATION: X7 can be D or T
<220> FEATURE:
<221> NAME/KEY: VARIANT
<222> LOCATION: (31)..(31)
<223> OTHER INFORMATION: X8 can be F or W
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: VARIANT
```

-continued

```
<222> LOCATION: (45)..(45)
<223> OTHER INFORMATION: X10 can be R or P
<220> FEATURE:
<221> NAME/KEY: VARIANT
<222> LOCATION: (45)..(45)
<223> OTHER INFORMATION: X10 can be R or P
<220> FEATURE:
<221> NAME/KEY: VARIANT
<222> LOCATION: (48)..(48)
<223> OTHER INFORMATION: X11 can be F or Y
<220> FEATURE:
<221> NAME/KEY: VARIANT
<222> LOCATION: (49)..(49)
<223> OTHER INFORMATION: X12 can be R or A
<220> FEATURE:
<221> NAME/KEY: VARIANT
<222> LOCATION: (50)..(50)
<223> OTHER INFORMATION: X13 can be T or A
<220> FEATURE:
<221> NAME/KEY: VARIANT
<222> LOCATION: (58)..(58)
<223> OTHER INFORMATION: X14 can be S or P
<220> FEATURE:
<221> NAME/KEY: VARIANT
<222> LOCATION: (69)..(69)
<223> OTHER INFORMATION: X15 can be E or D
<220> FEATURE:
<221> NAME/KEY: VARIANT
<222> LOCATION: (76)..(76)
<223> OTHER INFORMATION: X16 can be N or S
<220> FEATURE:
<221> NAME/KEY: VARIANT
<222> LOCATION: (78)..(78)
<223> OTHER INFORMATION: X17 can be R or Q
<220> FEATURE:
<221> NAME/KEY: VARIANT
<222> LOCATION: (88)..(88)
<223> OTHER INFORMATION: X18 can be L or Q
<220> FEATURE:
<221> NAME/KEY: VARIANT
<222> LOCATION: (90)..(90)
<223> OTHER INFORMATION: X19 can be H or Y
<220> FEATURE:
<221> NAME/KEY: VARIANT
<222> LOCATION: (91)..(91)
<223> OTHER INFORMATION: X20 can be S or K
<220> FEATURE:
<221> NAME/KEY: VARIANT
<222> LOCATION: (92)..(92)
<223> OTHER INFORMATION: X21 can be S or H
<220> FEATURE:
<221> NAME/KEY: VARIANT
<222> LOCATION: (95)..(95)
<223> OTHER INFORMATION: X22 can be P or L
<220> FEATURE:
<221> NAME/KEY: VARIANT
<222> LOCATION: (99)..(99)
<223> OTHER INFORMATION: X23 can be Q or G
<220> FEATURE:
<221> NAME/KEY: VARIANT
<222> LOCATION: (103)..(103)
<223> OTHER INFORMATION: X24 can be L or V
<220> FEATURE:
<221> NAME/KEY: VARIANT
<222> LOCATION: (106)..(106)
<223> OTHER INFORMATION: X25 can be S or K

<400> SEQUENCE: 2

Xaa Xaa Xaa Thr Gln Ser Pro Ser Ser Leu Ser Ala Ser Val Gly Xaa
 1               5                  10                  15

Arg Val Xaa Ile Thr Cys Arg Ala Ser Gln Asp Xaa Asn Xaa Xaa Leu
            20                  25                  30

Ala Trp Xaa Gln Gln Lys Pro Gly Lys Ala Pro Lys Xaa Leu Ile Xaa
        35                  40                  45

Xaa Xaa Ser Ser Leu Gln Gly Gly Val Xaa Ser Arg Phe Ser Gly Ser
50                  55                  60
```

```
Gly Ser Gly Thr Xaa Phe Thr Leu Thr Ile Ser Xaa Leu Xaa Pro Glu
 65                  70                  75                  80

Asp Phe Ala Thr Tyr Tyr Cys Xaa Gln Xaa Xaa Xaa Tyr Pro Xaa Thr
                 85                  90                  95

Phe Gly Xaa Gly Thr Lys Xaa Glu Ile Xaa Arg Thr
            100                 105

<210> SEQ ID NO 3
<211> LENGTH: 121
<212> TYPE: PRT
<213> ORGANISM: Pan troglodytes

<400> SEQUENCE: 3

Leu Glu Glu Ser Gly Gly Gly Leu Val Lys Pro Gly Asp Ser Leu Arg
 1               5                  10                  15

Leu Ser Cys Ala Ala Ser Gly Phe Thr Phe Ser Val Tyr Ala Met His
             20                  25                  30

Trp Val Arg Gln Ala Pro Glu Lys Gly Leu Glu Trp Val Ser Thr Ile
             35                  40                  45

Gly Ala Gly Gly Asn Thr Trp His Ser Asp Ser Val Lys Gly Arg Tyr
 50                  55                  60

Thr Ile Ala Arg Asp Asn Ser Gln Asn Thr Leu Ser Leu Gln Met Asn
 65                  70                  75                  80

Ser Leu Arg Ala Glu Asp Thr Ala Val Tyr Tyr Cys Val Arg Gly
                 85                  90                  95

Tyr Cys Ser Ser Thr Arg Cys Asp Ser Asn Asp Ala Phe Asp Ile Trp
                100                 105                 110

Gly Gln Gly Thr Met Val Thr Val Ser
        115                 120

<210> SEQ ID NO 4
<211> LENGTH: 108
<212> TYPE: PRT
<213> ORGANISM: Pan troglodytes

<400> SEQUENCE: 4

Ala Pro Met Thr Gln Ser Pro Ser Ser Leu Ser Ala Ser Val Gly Asp
 1               5                  10                  15

Arg Val Ser Ile Thr Cys Arg Ala Ser Gln Asp Ile Asn Asp Phe Leu
             20                  25                  30

Ala Trp Phe Gln Gln Lys Pro Gly Lys Ala Pro Lys Arg Leu Ile Phe
             35                  40                  45

Arg Thr Ser Ser Leu Gln Gly Gly Val Ser Ser Arg Phe Ser Gly Ser
 50                  55                  60

Gly Ser Gly Thr Glu Phe Thr Leu Thr Ile Ser Asn Leu Arg Pro Glu
 65                  70                  75                  80

Asp Phe Ala Thr Tyr Tyr Cys Leu Gln His Ser Ser Tyr Pro Pro Thr
                 85                  90                  95

Phe Gly Gln Gly Thr Lys Leu Glu Ile Ser Arg Thr
            100                 105

<210> SEQ ID NO 5
<211> LENGTH: 120
<212> TYPE: PRT
<213> ORGANISM: Pan troglodytes

<400> SEQUENCE: 5

Leu Glu Ser Gly Gly Gly Leu Val Lys Pro Gly Gly Ser Leu Thr Leu
```

```
                1               5                  10                  15
Ser Cys Ala Ala Ser Gly Phe Thr Phe Ser Thr Tyr Ala Met His Trp
                    20                  25                  30

Val Arg Gln Ala Pro Glu Lys Gly Leu Glu Trp Val Ser Thr Ile Gly
            35                  40                  45

Arg Ser Gly Asp Thr Leu Tyr Ser Asp Ser Val Lys Gly Arg Phe Ser
        50                  55                  60

Ile Ser Arg Asp Asn Ser Lys Asn Thr Leu Tyr Leu Gln Met Asn Ser
65                  70                  75                  80

Leu Arg Ala Glu Asp Thr Ala Val Tyr Tyr Cys Ala Arg Lys Gly Tyr
                85                  90                  95

Cys Ser Ser Thr Asn Cys Gln Ser Gln Tyr Tyr Phe Asp Tyr Trp Gly
                    100                 105                 110

Gln Gly Thr Leu Val Thr Val Ser
            115                 120

<210> SEQ ID NO 6
<211> LENGTH: 107
<212> TYPE: PRT
<213> ORGANISM: Pan troglodytes

<400> SEQUENCE: 6

Glu Leu Thr Gln Ser Pro Ser Ser Leu Ser Ala Ser Val Gly Gly Arg
1               5                   10                  15

Val Thr Ile Thr Cys Arg Ala Ser Gln Asp Val Asn Thr Trp Leu Ala
                    20                  25                  30

Trp Tyr Gln Gln Lys Pro Gly Lys Ala Pro Lys Pro Leu Ile Tyr Ala
            35                  40                  45

Ala Ser Ser Leu Gln Gly Gly Val Pro Ser Arg Phe Ser Gly Ser Gly
        50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Tyr Lys His Tyr Pro Leu Thr Phe
                85                  90                  95

Gly Gly Gly Thr Lys Val Glu Ile Lys Arg Thr
            100                 105

<210> SEQ ID NO 7
<211> LENGTH: 363
<212> TYPE: DNA
<213> ORGANISM: Pan troglodytes

<400> SEQUENCE: 7
ctcgaggagt ctgggggagg cctggtaaag cctggggatt ccctgagact ctcgtgtgca      60
gcctctggat tcaccttcag tgtctatgct atgcactggg tccgccaggc tccagagaag     120
gggctggagt gggtctcaac tattggtgct ggtggtaata cgtggcactc cgactctgtc     180
aagggccgat acaccattgc cagagacaat tcccagaata cgctgtctct gcaaatgaac     240
agcctgagag ccgaggacac ggccgtgtat tactgtgtga aggggggata ctgtagcagt     300
actaggtgcg acagtaatga tgcttttgat atctggggcc aagggacaat ggtcaccgtc     360
tct                                                                   363

<210> SEQ ID NO 8
<211> LENGTH: 324
<212> TYPE: DNA
<213> ORGANISM: Pan troglodytes
```

-continued

```
<400> SEQUENCE: 8
gctccgatga cccagtctcc atcctcattg tctgcatctg tgggagacag agtcagcatc    60
acttgtcggg cgagtcagga cattaacgat ttttggcct ggtttcagca gaaaccaggg   120
aaagccccta agcgtctgat ctttcgtact tccagtttgc aaggtggagt ctcatcaaga   180
ttcagtggca gtggatctgg gacagaattc actctcacaa tcagcaacct gcggcctgaa   240
gattttgcaa cttattactg tctgcagcat agttcttacc ctccgacctt cggccaaggg   300
accaaactgg agatcagccg aact                                          324

<210> SEQ ID NO 9
<211> LENGTH: 360
<212> TYPE: DNA
<213> ORGANISM: Pan troglodytes

<400> SEQUENCE: 9
ctcgagtctg ggggaggctt ggtcaagccg ggggggtccc tgacactctc gtgtgcagcc    60
tctggattca ccttcagtac ctatgctatg cactgggtcc gccaggctcc agagaagggg   120
ctggagtggg tctcaactat tggtcgtagt ggtgacacgt tgtactcaga ctctgtcaag   180
ggccgattca gcatctccag agacaattcc aagaacaccc tgtatctgca aatgaacagc   240
ctgagagccg aggacacggc cgtgtattat tgtgcgagaa agggatattg tagtagtacc   300
aactgtcagt cccaatatta ctttgactac tggggccagg gaaccctggt caccgtctcc   360

<210> SEQ ID NO 10
<211> LENGTH: 321
<212> TYPE: DNA
<213> ORGANISM: Pan troglodytes

<400> SEQUENCE: 10
gagctcaccc agtctccatc ctcactgtct gcatctgtgg gaggcagagt caccatcact    60
tgtcgggcca gtcaggatgt taacacctgg ttagcctggt atcagcagaa accagggaaa   120
gcccctaagc ccctgatcta tgctgcatcc agtttgcaag gtggggtccc atcaaggttt   180
agcggcagtg gtctgggac agatttcact ctaaccatca gcagcctgca gcctgaagat   240
tttgcaactt attactgcca acaatataaa cattaccctc tcactttcgg tggagggacc   300
aaggtggaga tcaaacgaac t                                             321

<210> SEQ ID NO 11
<211> LENGTH: 23
<212> TYPE: PRT
<213> ORGANISM: Homo sapiens

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 12
<211> LENGTH: 14
<212> TYPE: PRT
<213> ORGANISM: Homo sapiens

<400> SEQUENCE: 12

Trp Tyr Gln Gln Lys Pro Gly Gln Pro Pro Leu Leu Ile Tyr
1               5                   10
```

```
<210> SEQ ID NO 13
<211> LENGTH: 32
<212> TYPE: PRT
<213> ORGANISM: Homo sapiens

<400> SEQUENCE: 13

Gly Val Pro Asp Arg Pro Phe Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 14
<211> LENGTH: 11
<212> TYPE: PRT
<213> ORGANISM: Homo sapiens

<400> SEQUENCE: 14

Phe Gly Gln Gly Gln Thr Lys Leu Glu Ile Lys
1               5                   10

<210> SEQ ID NO 15
<211> LENGTH: 30
<212> TYPE: PRT
<213> ORGANISM: Homo sapiens

<400> SEQUENCE: 15

Gln Val Gln Leu Val Gln Ser Gly Ala Glu Val Lys Lys Pro Gln Ala
1               5                   10                  15

Ser Val Lys Val Ser Cys Lys Ala Ser Gln Tyr Thr Phe Thr
            20                  25                  30

<210> SEQ ID NO 16
<211> LENGTH: 14
<212> TYPE: PRT
<213> ORGANISM: Homo sapiens

<400> SEQUENCE: 16

Trp Val Arg Gln Ala Pro Gly Gln Arg Leu Glu Trp Met Gly
1               5                   10

<210> SEQ ID NO 17
<211> LENGTH: 32
<212> TYPE: PRT
<213> ORGANISM: Homo sapiens

<400> SEQUENCE: 17

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 18
<211> LENGTH: 11
<212> TYPE: PRT
<213> ORGANISM: Homo sapiens

<400> SEQUENCE: 18

Trp Gly Gln Gly Thr Leu Val Thr Val Ser Ser
1               5                   10
```

MONOCLONAL ANTIBODIES THAT REACT WITH THE CAPSULE OF *BACILLUS ANTHRACIS*

CROSS REFERENCE TO RELATED APPLICATIONS

This is the U.S. National Stage of International Application No. PCT/US2009/065198, filed Nov. 19, 2009, which was published in English under PCT Article 21(2), which in turn claims the benefit of U.S. Provisional Application No. 61/116,222, filed Nov. 19, 2008, which is incorporated herein by reference.

FIELD OF THE DISCLOSURE

This application relates to the field of antibodies, specifically to human antibodies that specifically bind the capsule of *Bacillus anthracis* and their use.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Apr. 6, 2011, and having a size of 14.3 kilobytes, as permitted under 37 CFR 1.821(c). The material in the aforementioned file is hereby incorporated by reference in its entirety.

BACKGROUND

Anthrax is a potentially lethal human infection. The pathogen responsible for anthrax is the Gram-positive rod-shaped bacterium, *Bacillus anthracis* (*B. anthracis*). In many situations, the body protects against pathogenic infections by producing antibodies that bind to antigens on the pathogen to facilitate the removal or "clearance" of the pathogens by a process called phagocytosis, wherein phagocytic cells (for example neutrophils and macrophages) identify, engulf, and subsequently destroy the pathogens. However, some pathogens, such as *B. anthracis*, avoid phagocytosis by encapsulating themselves with a capsule that is poorly immunogenic and has antiphagocytic properties.

The virulence of *B. anthracis* is dependent on anthrax toxin (AT) and the poly-γ-D-glutamic acid (γDPGA) capsule. γDPGA is poorly immunogenic and does not induce booster responses. In addition, the γDPGA capsule shields the vegetative form of *B. anthracis* from agglutination by monoclonal antibodies to its cell wall polysaccharide. Thus, few effective antibody therapies directed against *B. anthracis* have been developed. Accordingly, there is an ongoing need to develop therapeutics to combat anthrax infection.

SUMMARY

Opsonins cause microorganisms to be more susceptible to phagocytosis and interfere with the protective properties of a bacterial capsule by binding to target antigens on the bacterial surface. This process is called opsonization. Opsonins, which include antibodies and complement proteins such as C3a and C5a, have lytic activities and can enhance the rate of clearance of a microorganism from the bloodstream. Antibodies which enhance opsonophagocytosis of the microorganism *Bacillus anthracis* are disclosed herein.

Isolated chimpanzee monoclonal antibodies 4C and 11D, and chimeric forms thereof, humanized forms thereof, or functional fragments thereof are disclosed. Also disclosed is a consensus anti-γDPGA chimpanzee monoclonal antibody. The 4C and 11D monoclonal antibodies specifically bind γDPGA present on the cell surface of *B. anthracis*. In some examples, the chimeric forms of these antibodies, humanized forms of these antibodies, and functional fragments of these antibodies include the specificity determining regions (SDRs) and/or the complementarity determining regions (CDRs) of the 4C monoclonal antibody, the 11D monoclonal antibody or the disclosed consensus anti-γDPGA chimpanzee monoclonal antibody. The monoclonal antibodies, chimeric forms, humanized forms or functional fragments thereof can be conjugated to an effector molecule, such as a detectable marker, a therapeutic agent, or a toxin. Also disclosed are nucleic acid molecules encoding these disclosed antibodies. In addition, kits for detecting *B. anthracis* in a sample are disclosed herein.

Methods are disclosed for detecting *B. anthracis*. Such methods include contacting a biological sample with one of the disclosed antibodies, a chimeric form thereof, a humanized form thereof, or a functional fragment thereof, under conditions wherein an immune complex will form, and detecting the formation of the immune complex. The detection of an immune complex indicates the presence of *B. anthracis*.

Methods for treating or inhibiting *B. anthracis* infection are also disclosed. The disclosed methods include administering to a subject an effective amount of one or more of the disclosed antibodies, a chimeric form thereof, a humanized form thereof, or a functional fragment thereof, thereby inhibiting the *B. anthracis* infection.

Also provided herein are methods of enhancing opsonophagocytosis of *B. anthracis* in a subject. The method includes selecting for treatment a subject who is at risk for developing a *B. anthracis* infection or is infected by *B. anthracis* and administering a therapeutically effective amount of one or more of the disclosed antibodies, a chimeric form thereof, a humanized form thereof, or a functional fragment thereof, thereby enhancing the opsonophagocytosis of *B. anthracis*.

The foregoing and other features and advantages will become more apparent from the following detailed description of several embodiments, which proceeds with reference to the accompanying figures.

BRIEF DESCRIPTION OF THE FIGURES

FIG. 1A is an alignment of the amino acid sequence of the heavy chain of the anti-γDPGA monoclonal antibodies (mAbs) 4C and 11D. The figure shows the alignment of the sequence of the 4C antibody heavy chain (top; SEQ ID NO: 3) with the sequence of the 11D antibody heavy chain (below; SEQ ID NO: 5). Identical residues are identified by a dot (.); missing residues are identified by a dash (-). The location of the framework regions and the complementarity determining regions (CDRs) are also shown.

FIG. 1B is an alignment of the amino acid sequence of the light chain of the anti-γDPGA monoclonal antibodies 4C and 11D. The figure shows the alignment of the sequence of the 4C antibody light chain (top; SEQ ID NO: 4) with the sequence of the 11D antibody light chain (below; SEQ ID NO: 6). Identical residues are identified by a dot (.); missing residues are identified by a dash (-). The location of the framework regions and the complementarity determining regions (CDRs) are also shown.

FIG. 3 is a set of digital images of a capsular quellung type reaction using the 4C monoclonal antibody. Cells of formalin-killed *B. anthracis* (Ames 34 strain) were incubated with IgG1 of anti-γDPGA 4C monoclonal antibody at concentrations of 25 μg/ml (FIG. 3C), 50 μg/ml (FIG. 3D), and 100 μg/ml (FIG. 3E). The Fab of anti-γDPGA ml (FIG. 3B) or IgG1 of anti-PA ml (FIG. 3A) at 100 μg/ml were used as controls. The reactions were assessed by DIC microscopy and show that IgG1 of anti-γDPGA at concentrations of 50 μg/ml and 100 μg/ml produced a rim type reaction at the capsule perimeter of formalin-killed *B. anthracis* (Ames 34 strain).

BIOLOGICAL DEPOSIT

Figure 2:
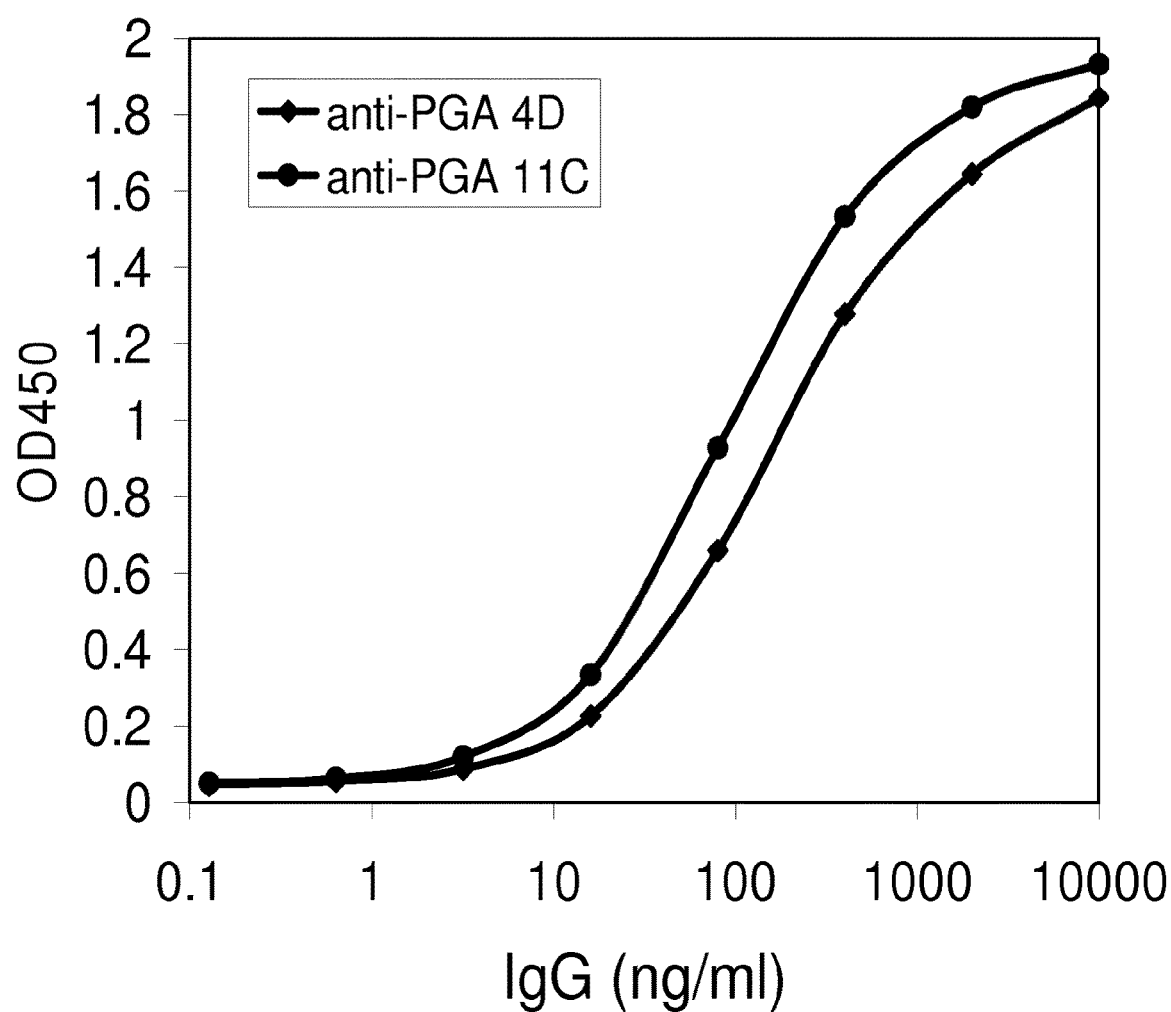
FIG. 2 is as a graph of an exemplary binding curve of the 4C and 11D anti-γDPGA monoclonal antibodies converted to full-length IgG with human γ1 constant regions, showing the binding of these antibodies to γDPGA as measured by an enzyme-linked immunosorbent assay (ELISA).
Figure 4A:
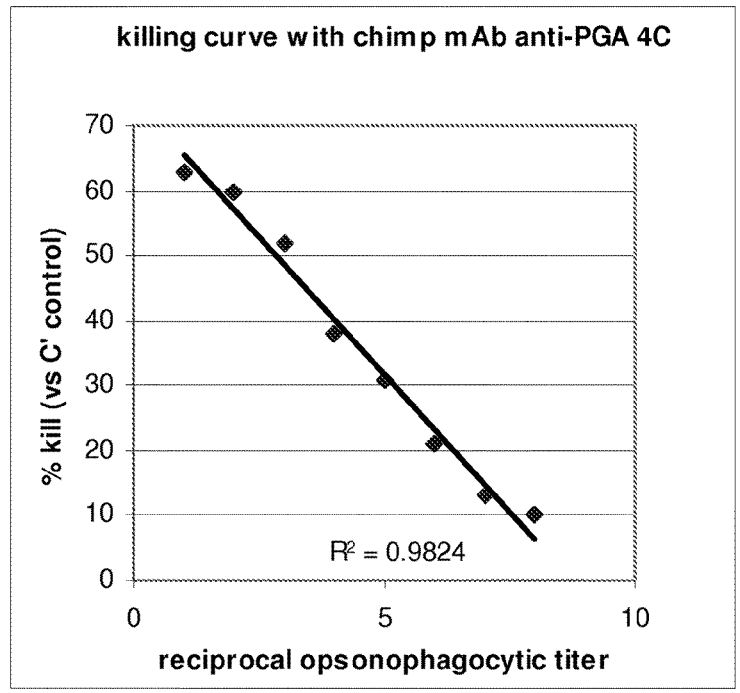
FIG. 4 is a set of graphs showing the opsonophagocytic activity of anti-γDPGA monoclonal antibodies 4C (FIG. 4A) and 11D (FIG. 4B) as measured by their ability to kill *B. anthracis* cells in the presence of human polymorphonuclear leukocytes and complement. Opsonophagocytosis was defined as ≧50% killing compared with growth in control (no antibody) wells.
Figure 4B:
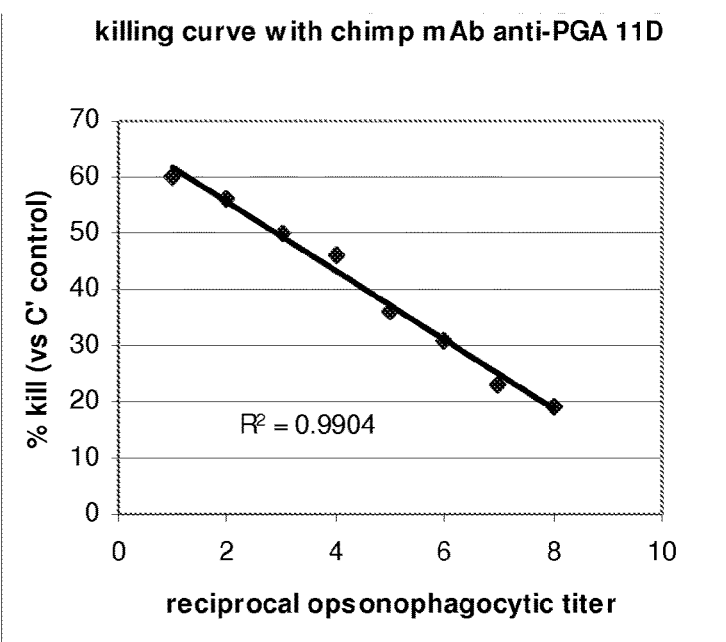

Plasmids containing DNA encoding the monoclonal antibodies 4C and 11D were deposited in accordance with the Budapest Treaty with the American Type Culture Collection (ATCC) Patent Depository, 10801 University Blvd., Manassas, Va., 20110, on Nov. 14, 2008. The plasmid pComb3H-4C encoding the 4C FAb sequence was deposited as Accession No. PTA-9610. The plasmid pComb3H-11D encoding the 11D Fab sequence was deposited as Accession Nos. PTA-9609.

Sequence Listing

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is the consensus sequence of an anti-γDPGA antibody heavy chain.

SEQ ID NO: 2 is the consensus sequence of an anti-γDPGA antibody light chain.

SEQ ID NO: 3 is an exemplary amino acid sequence of a 4C monoclonal antibody heavy chain.

SEQ ID NO: 4 is an exemplary amino acid sequence of a 4C monoclonal antibody light chain.

SEQ ID NO: 5 is an exemplary amino acid sequence of an 11D monoclonal antibody heavy chain.

SEQ ID NO: 6 is an exemplary amino acid sequence of an 11D monoclonal antibody light chain.

SEQ ID NO: 7 is an exemplary nucleic acid sequence encoding a 4C monoclonal antibody heavy chain.

SEQ ID NO: 8 is an exemplary nucleic acid sequence encoding a 4C monoclonal antibody light chain.

SEQ ID NO: 9 is an exemplary nucleic acid sequence encoding an 11D monoclonal antibody heavy chain.

SEQ ID NO: 10 is an exemplary nucleic acid sequence encoding an 11D monoclonal antibody light chain.

SEQ ID NOs: 11-18 are exemplary amino acid sequences of human framework regions.

DETAILED DESCRIPTION

I. Abbreviations

AT Anthrax toxin
ATR Anthrax toxin receptor
CDR Complementarity determining region
$C_H$ Heavy chain constant region
$C_L$ Light chain constant region
EF Edema factor
EM Effector moiety/molecule
ELISA Enzyme linked immunosorbant assay
Fab Fragment, antigen binding
FACS Fluorescence activated cell sorting
Fc Fragment, crystallizable
FITC fluorescein isothiocyanate
γ-DPGA Poly-γ-D-glutamic acid
HRP Horseradish peroxidase
LF Lethal factor
LeTx Lethal toxin
mAb Monoclonal antibody
PA Protective antigen
PE Phycoerythrin
PNAs Peptide nucleic acids
RIA Radioimmunoassay
SDR Specificity determining region
T Threonine
V Valinr
VH Variable heavy
VL Variable light
YFP Yellow fluorescent protein II. Summary of Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

As used herein, the singular forms "a," "an," and "the," refer to both the singular as well as plural, unless the context clearly indicates otherwise. For example, the term "antibody" includes single or plural antibodies and can be considered equivalent to the phrase "at least one antibody."

As used herein, the term "comprises" means "includes." Thus, "comprising an antibody" means "including an antibody" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Administration:

The introduction of a composition into a subject by a chosen route. For example, if the chosen route is intravenous, the composition is administered by introducing the composition into a vein of the subject. In some examples an antibody or antibody fragment, such as those described herein, is administered.

Amplification:

Refers to use of a technique that increases the number of copies of a nucleic acid molecule in a sample, for example the amplification of a nucleic acid that encodes the monoclonal antibody 4C or 11D, a chimeric form thereof, a humanized form thereof, or a fragment thereof. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European patent publication No. EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal:

Living multi-cellular vertebrate organisms, a category that includes, for example, mammals and birds. The term mammal includes both human and non-human mammals. Similarly, the term "subject" includes both human and veterinary subjects.

Antibody:

A polypeptide ligand comprising at least a light chain or heavy chain immunoglobulin variable region which specifically recognizes and binds an epitope of an antigen or a fragment thereof. Antibodies can be composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

The term antibody includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, an antibody with non-human variable regions and human constant regions or with a non-human Fab region and a human Fc region), humanized antibodies (for example, an antibody with non-human SDRs and/or CDRs and human framework regions), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds an antigen of interest has a specific $V_H$ region and the $V_L$ region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of a hybridoma generated from a B-lymphocyte and a myeloma cell, or by a cell transfected with the light and heavy chain genes of a single antibody, or by the progeny thereof. The preparation of monoclonal antibodies is conventional. See, for example, Kohler & Milstein, *Nature* 256:495, 1975; Coligan et al., sections 2.5.1-2.6.7; and Harlow et al., *Antibodies: A Laboratory Manual*, p. 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Hybridoma cells, and their progeny, that secrete monoclonal antibodies are also encompassed by this disclosure. Monoclonal antibodies include chimpanzee, human, and humanized monoclonal antibodies, such as humanized chimpanzee monoclonal antibodies. In some examples, a monoclonal antibody is the monoclonal antibody 4C or 11D or a consensus anti-γDPGA monoclonal antibody.

A "consensus monoclonal antibody" has a consensus light chain amino acid sequence and a consensus heavy chain amino acid sequence, wherein each consensus amino acid sequence represents the results of multiple sequence alignments of related sequences and the consensus sequence shows amino acid residues that are common among the aligned sequences. Common residues in the consensus light chain and heavy chain sequences are conserved amino acids and are generally important for antigen binding. The residues that vary among the aligned sequences represent amino acid positions that can tolerate sequence variability and are generally not important for antigen binding.

A "chimeric antibody" is an antibody that includes sequences derived from two different antibodies, which typically are of different species. Chimeric antibodies generally include human constant regions and variable regions from other animal sources, such as chimpanzees, for example chimpanzee Fab regions, CDRs, and/or chimpanzee SDRs. In some examples, a chimeric antibody includes the Fab region from a chimpanzee antibody and an Fc region from a human antibody. In particular examples a chimeric antibody includes the SDRs or CDRs from a chimpanzee antibody.

A "humanized" antibody immunoglobulin is an immunoglobulin including a human variable framework region and one or more CDRs and/or SDRs from a non-human (for example a chimpanzee, mouse, rat, or synthetic) immunoglobulin. The non-human immunoglobulin providing the CDRs or SDRs is termed a "donor," and the human immunoglobulin providing the variable framework region is termed an "acceptor." In one embodiment, all the CDRs are from the donor immunoglobulin in a humanized antibody. In another embodiment, only SDRs are from the donor immunoglobulin in a humanized antibody. Constant regions need not be present, but if they are, they must be substantially identical to human immunoglobulin constant regions, such as at least about 85-90%, such as about 95% or more identical. Hence, in one embodiment, all parts of a humanized immunoglobulin, except possibly one or more CDRs and/or SDRs, are substantially identical to corresponding parts of natural human immunoglobulin sequences. In one embodiment, a "humanized antibody" is an antibody comprising a humanized light chain and a humanized heavy chain immunoglobulin. A humanized antibody binds to the same antigen as the donor antibody that provides the CDRs or SDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Bacillus:

A genus of bacteria whose characteristics include the ability to degrade of most substrates derived from plant and animal sources, including cellulose, starch, pectin, proteins, agar, hydrocarbons, and others; antibiotic production; nitrification; denitrification; nitrogen fixation; facultative lithotrophy; autotrophy; acidophily; alkaliphily; psychrophily, thermophily and parasitism. Spore formation, a universal characteristic of the genus, is thought to be a strategy for Bacillus survival in the soil environment, wherein this genus of bacteria predominate. Aerial distribution of dormant spores likely explains the occurrence of Bacillus species in most habitats examined.

There are more than 40 recognized species in the genus Bacillus (Bergey's Manual of Systematic Bacteriology Vol. 2 (1986)). These include, but are not limited to, B. acidocaldarius, B. alkalophilus, B. alvei, B. anthracis, B. azotoformans, B. badius, B. brevis, B. cereus, B. circulans, B. coagulans, B. fastidiosis, B. firmus, B. globisporus, B. insolitus, B. larvae, B. laterosporus, B. lentimorbus, B. lentus, B. licheniformis, B. macerans, B. macquariensis, B. marinus, B. megaterium, B. mycoides, B. pantothenticus, B. pasteurii, B. polymyxa, B. popillia, B. pumilus, B. schlegelii, B. sphaericus, B. stearothermophilus, B. subtilis, and B. thuringiensis. In one specific, non-limiting example, a Bacillus is Bacillus anthracis, the agent that causes anthrax.

Bacillus Anthracis:

The etiologic agent of anthrax, Bacillus anthracis is a large, gram-positive, nonmotile, spore-forming bacterial rod. The virulence of B. anthracis is dependent on anthrax toxin (AT), and the γDPGA capsule. The genes for the toxin, and the capsule, are carried by plasmids, designated pX01 and pX02, respectively (Mikesell et al., Infect. Immun. 39:371-76, 1983; Vodkin et al., Cell 34:693-97, 1983; Green et al., Infect. Immun. 49:291-97, 1985).

AT is composed of three entities: protective antigen (PA; the binding subunit of AT), and two enzymes known as lethal factor (LF) and edema factor (EF) (Mikesell et al., Infect. Immun. 39:371-76, 1983; Vodkin et al., Cell 34:693-97, 1983). PA is an 83 kDa protein that is the main protective constituent of anthrax vaccines. PA binds to the anthrax toxin receptor (ATR) on cells and is then proteolytically cleaved by the enzyme furin with release of a 20 kDa fragment (Bradley et al., Nature 414:225-29, 2001; Klimpel et al., PNAS 89:10277-81, 1992). The 63 kDa PA remnant ($PA_{63}$) features a second binding domain and binds to either EF (an 89 kDa protein) to form edema toxin, or LF (a 90 kDa protein) to form lethal toxin (LeTx) (Leppla et al., Salisbury Med. Bull. Suppl. 68:41-43, 1990). The resulting complex is internalized into the cell within endosomes (Singh et al., Infect. Immun. 67:1853-59, 1999; Friedlander, J. Biol. Chem. 261:7123-26, 1986).

The γDPGA capsule of B. anthracis serves as an essential virulence factor during anthrax infection, inhibiting host defense mechanisms through inhibition of phagocytosis of microorganism by macrophages. While other Bacillus produce γPGA in a mixture of both D- and L-forms, only B. anthracis is known to synthesize it exclusively in a D-conformation (Kovács et al., J. Chem. Soc. 4255-59, 1952). When injected, γDPGA has been shown to be a poor immunogen (Eisner, Schweiz. Z. Pathol. Bakteriol. 22:129-44, 1959; Ostroff et al., Proc. Soc. Exp. Biol. Med. 99:345-47, 1958). The capsule also shields the vegetative form of B. anthracis from agglutination by monoclonal antibodies to its cell wall polysaccharide (Ezzell et al., J. Clin. Microbiol. 28:223-31, 1990).

Binding Affinity:

Affinity of an antibody, such as the monoclonal antibody 4C or 11D, for an antigen, such as an antigen on the surface of B. anthracis for example γDPGA. In one embodiment, affinity is calculated by a modification of the Scatchard method described by Frankel et al., Mol. Immunol., 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$ M, at least about $2.0 \times 10^{-8}$ M, at least about $2.5 \times 10^{-8}$ M, at least about $3.0 \times 10^{-}$ sM, at least about $3.5 \times 10^{-8}$ M, at least about $4.0 \times 10^{-8}$ M, at least about $4.5 \times 10^{-8}$ M, or at least about $5.0 \times 10^{-8}$ M.

Complement:

A plasma protein system involved in immune defense. Following activation by antigen-antibody complexes, complement proteins lyse antigenic cells, attract phagocytic cells, and assist in the destruction of antigenic cells by opsonophagocytosis. In mammals, the complement system is made up of a series of about 25 proteins that work to "complement" the activity of antibodies in destroying bacteria, either by facilitating opsonophagocytosis or by puncturing the bacterial cell membrane. Complement also helps to rid the body of antigen-opsonic antibody complexes, for example by clearance of a pathogen that is bound by the opsonic antibody.

Complement proteins circulate in the blood in an inactive form until the first of the complement substances is triggered—usually by an antibody interlocked with an antigen. As each complement protein is activated, it acts upon another complement protein in a precise sequence of carefully regulated steps known as the "complement cascade."

Complement fragments (such as C3a, C3b, iC3b, C3d, C4b, or C5a, which become bound to antigen during complement activation) trigger opsonophagocytosis by binding to specific cell-surface receptors (such as Fc receptors and C3b receptors on neutrophils and macrophages, and C3d receptors on macrophages).

Complementarity Determining Region (CDR):

Amino acid sequences which together define the binding affinity and specificity of the natural Fv region of a native Ig binding site. The light and heavy chains of an immunoglobulin each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest, 5th* Edition, U.S. Department of Health and Human Services, Public Health Service, National Institutes of Health, Bethesda, Md. (NIH Publication No. 91-3242). CDRs contain the specificity determining regions (SDRs) of the antibody. In some examples, a CDR is a CDR from the monoclonal antibody 4C. In some examples, a CDR is a CDR from the monoclonal antibody 11D. In some examples, a CDR is a CDR from the consensus anti-γDPGA chimpanzee monoclonal antibody.

Conservative Variants:

Amino acid substitutions that do not substantially affect or decrease the affinity of an antibody to *B. anthracis* capsule. For example, an antibody that specifically binds *B. anthracis* capsule (such as the antibodies 4C or 11D, the consensus anti-γDPGA chimpanzee monoclonal antibody a chimeric form, or humanized form or a fragment thereof) can include at most about 1, at most about 2, at most about 5, and most about 10, or at most about 15 conservative substitutions and specifically bind the original anthrax capsule. The term conservative variation also includes the use of a substituted amino acid in place of an unsubstituted parent amino acid, provided that antibody specifically binds *B. anthracis* capsule.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting:

Placement in direct physical association. Such physical associations can be between solids, liquids, or solids and liquids.

Degenerate Variant:

A polynucleotide encoding an antibody that binds anthrax capsule that includes a sequence that is degenerate as a result of the genetic code. There are 20 natural amino acids, most of which are specified by more than one codon. Therefore, all degenerate nucleotide sequences are included as long as the amino acid sequence of the antibody that binds *B. anthracis* capsule encoded by the nucleotide sequence is unchanged.

Effective Amount or Therapeutically Effective Amount:

The amount of agent, such as the disclosed antibodies, the chimeric forms thereof, the humanized forms thereof, or the antibody fragments thereof, that is an amount sufficient to prevent (including prophylaxis), treat, reduce, and/or ameliorate the symptoms and/or underlying causes of any of a disorder or disease, for example to prevent, inhibit, and/or treat an infection with *B. anthracis*. In some embodiments, an "effective amount" or a "therapeutically effective amount" is an amount sufficient to reduce or eliminate a symptom of a disease, such as anthrax.

Effector Cells:

In one embodiment, effector cells are cells capable of binding to antibody/antigen complexes and internalizing such complexes. The complexes can be bound to a cell, microbe, or pathogen such that the cell, microbe, or pathogen is also internalized by the effector cell. In particular examples, effector cells express Fc receptors, such as FcγRI, FcγRII and FcγRIII that bind to antibody/antigen complexes and facilitate internalization. In some examples, effector cells are derived from the serum of an individual (such as peripheral blood leukocytes, PBLs) or from an in vitro culture. Examples of effector cells include, but are not limited to: macrophages, mononuclear phagocytes, natural killer cells, and granulocytes such as neutrophils and eosinophils.

Effector Molecule:

The portion of a molecule, for example a chimeric molecule that includes a disclosed antibody or fragment thereof, that is intended to have a desired effect on a cell, such as a *B. anthracis* cell, to which the molecule is targeted. Effector molecules are also known as an effector moieties (EM), therapeutic agents, or diagnostic agents, or similar terms. In some embodiments, effector molecules can be diagnostic agents or moieties. Diagnostic agents or moieties include radioisotopes and other detectable labels. Detectable labels useful for such purposes are also well known in the art, and include radioactive isotopes such as $^{32}$P, $^{125}$I, and $^{131}$I, fluorophores, chemiluminescent agents, magnetic resonance imaging agents and enzymes.

Epitope:

An antigenic determinant, such as that on the capsule of *B. anthracis*. Epitopes or antigenic determinants are particular chemical groups or peptide sequences on a molecule that are antigenic and can elicit a specific immune response. An antibody specifically binds a particular antigenic epitope.

Expressed:

Translation of a nucleic acid into a protein. Proteins may be expressed and remain intracellular, become a component of the cell surface membrane, or be secreted into the extracellular matrix or medium. In some examples, a disclosed antibody or fragment thereof is expressed from a nucleic acid sequence, for example expressed from an expression vector.

Expression Control Sequences:

Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence, for example the transcription and translation of the nucleic acid sequence encoding a disclosed antibody or fragment thereof from an expression vector, for example from a host cell transformed with an expression vector. Expression control sequences can include appropriate promoters, enhancers, transcription terminators, a start codon (i.e., ATG) in front of a protein-encoding gene, splicing signal for introns, and maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, pap, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Framework Region:

Amino acid sequences interposed between CDRs, and includes variable light and variable heavy framework regions. The framework regions serve to hold the CDRs of an antibody or fragment thereof in an appropriate orientation for antigen binding. In some examples, a framework region is a human framework region. In some examples, a framework region is a chimpanzee framework region, such as framework region from the 4C or 11D monoclonal antibody or from the consensus anti-γDPGA chimpanzee monoclonal antibody.

Heterologous:

A heterologous sequence is a sequence that is not normally found adjacent to a second sequence. In one embodiment, the heterologous sequence is from a different genetic source, such as a virus or a different organism, than the second sequence. For example a nucleotide sequence encoding a 4C or 11D antibody or the consensus anti-γDPGA chimpanzee monoclonal antibody can be operably linked to a heterologous nucleotide sequence encoding a fluorescent molecule capable of detection, such as a fluorescent protein, for example green fluorescent protein (GFP).

Host Cells:

Cells in which a vector can be propagated and its DNA expressed, for example a vector encoding a disclosed antibody of fragment thereof. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. In some examples, a host cell propagates a vector encoding a 4C or 11D antibody, the consensus anti-DPGA chimpanzee monoclonal antibody, humanized form thereof, or chimeric form thereof, or functional fragment thereof.

Immunoconjugate:

A covalent linkage of an effector molecule to an antibody, such as a 4C or 11D antibody, the consensus anti-γDPGA chimpanzee monoclonal antibody, humanized form thereof, or chimeric form thereof, or functional fragment thereof. In some examples the effector molecule can be a detectable label. In one embodiment, an antibody linked (coupled) to an effector molecule is further linked to a lipid or other molecule to a protein or peptide to increase its half-life in the body. The linkage can be achieved either by chemical or recombinant means. When the linkage is chemical, a reaction between the antibody moiety and the effector molecule has produced a covalent bond formed between the two molecules to form one molecule. A peptide linker (short peptide sequence) can optionally be included between the antibody and the effector molecule. Because immunoconjugates are prepared from two molecules with separate functionalities, such as an antibody and an effector molecule, they are also sometimes referred to as "chimeric molecules." The term "chimeric molecule," as used with reference to an effector molecule, therefore refers to a targeting moiety, such as a ligand or an antibody, conjugated (coupled or covalently linked) to an effector molecule.

Immunologically Reactive Conditions:

Conditions in which an antibody raised against a particular epitope bind to that epitope (or to a cell expressing the epitope) to a detectably greater degree than, and/or to the substantial exclusion of, binding to substantially all other epitopes (or cells not expressing the epitope). Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or Treating a Pathological Condition or Disease:

Inhibiting the full or partial development of a disease or pathological condition, for example, in a subject who is at risk at being infected by *Bacillus anthracis* or who is at risk for a disease such as anthrax. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, or by other parameters well known in the art that are specific to the particular disease. A "prophylactic" treatment is a treatment administered to a subject who does not exhibit signs of a disease or condition, or exhibits only early signs of such. In one embodiment, a prophylactic treatment is administered for the purpose of decreasing the risk of developing a pathology associated with a disease or condition.

Isolated:

An "isolated" biological component (such as a nucleic acid, polypeptide, for example and antibody or fragment thereof (for example 4C, 11D antibody, or the consensus anti-γDPGA chimpanzee monoclonal antibody, a humanized form thereof, or a chimeric form thereof, or a functional fragment thereof), cell or protein) that has been substantially separated, produced apart from, or purified away from other biological components in the cell of the organism in which the component naturally occurs. Nucleic acids and polypeptides which have been "isolated" thus include nucleic acids and polypeptides purified by standard purification methods. The term also embraces nucleic acids and polypeptides prepared by recombinant expression in a host cell as well as chemically synthesized nucleic acids. A purified nucleic acid, polypeptide, cell, or cell component can be at least 90%, at least 95%, at least 96%, at least 97%, at least 98%, or at least 99% pure.

Label:

A detectable compound or composition that is conjugated directly or indirectly to another molecule, such as an antibody (for example a 4C or 11D antibody, a consensus anti-γDPGA chimpanzee monoclonal antibody, humanized form thereof, or chimeric form thereof, or functional fragment thereof) or a protein, to facilitate detection of that molecule. Specific, non-limiting examples of labels include detectable markers, such as fluorescent tags, enzymatic linkages, and radioactive isotopes. In specific, non-limiting embodiments, an amino acid is radiolabeled or a polypeptide is conjugated to biotinyl moieties that can be detected by marked avidin (for example, streptavidin containing a fluorescent marker or an enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors, fluorescent proteins, such as green fluorescent protein), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms or linkers of various lengths to reduce potential steric hindrance.

Linker Peptide:

A peptide within an antibody binding fragment (such as an Fv fragment, for example a 4C or 11D antibody fragment) which serves to indirectly bond the variable heavy chain to the variable light chain. "Linker" can also refer to a peptide serving to link a targeting moiety, such as a scFv, to an effector molecule, such as a detectable label.

The terms "conjugating," "joining," "bonding" or "linking" refer to making two polypeptides into one contiguous polypeptide molecule, or to covalently attaching a radionuclide or other molecule to a polypeptide, such as an antibody. In the specific context, the terms include reference to joining a molecule, such as an antibody moiety, to an effector molecule ("EM"). The linkage can be either by chemical or recombinant means. "Chemical means" refers to a chemical reaction between the antibody moiety and the effector molecule such that there is a covalent bond formed between the two molecules to form one molecule.

Nucleic Acid:

A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Non-naturally occurring synthetic analogs include, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom, for example an antibody, such as a 4C or 11D antibody, a consensus anti-γDPGA chimpanzee monoclonal antibody, or a portion of an antibody, such as $V_H$ or $V_L$ from a 4C or 11D antibody. Thus, a gene encodes a protein if transcription and translation of mRNA produced by that gene produces the protein in a cell or other biological system. Both the coding strand (the nucleotide sequence of which is identical to the mRNA sequence and is usually provided in sequence listings) and non-coding strand (used as the template for transcription) of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence (for example a coding sequence of an antibody or fragment therefore herein disclosed) if the promoter affects the transcription or expression of the coding sequence. Generally, operably linked DNA sequences are contiguous and, where necessary to join two protein coding regions, in the same reading frame.

Opsonin:

A molecule that becomes attached to the surface of a microbe or pathogen, such as a bacterial, fungal, or viral pathogen, that can be recognized by surface receptors of neutrophils and macrophages and that increases the efficiency of phagocytosis of the microbe or pathogen. Opsonins include IgG antibodies, which are recognized by the Fcγ receptor on phagocytes, and fragments of complement proteins, which are recognized by the cell surface protein CR1 (CD35) and by the leukocyte integrin Mac-1. Exemplary opsonins include opsonizing antibodies (IgM, IgG1, IgG2, IgG3 and IgA immunoglobulins specific for the antigen), such as a 4C or 11D antibody, humanized form thereof, or chimeric form thereof, or functional fragment thereof, and certain complement fragments (C3a, C3b, iC3b, C3d, C4b, or C5a, which become bound to the antigen during complement activation), both of which trigger phagocytosis by binding to specific cell-surface receptors (such as Fc receptors and C3b receptors on neutrophils and macrophages, and C3d receptors on macrophages). Opsonins include any substance that binds to particulate antigens on the surface of a cell and induces the phagocytosis of the cell by effector cells.

Opsonophagocytosis (Opsonization):

The process of enhancing the ability of effector cells (such as macrophages and monocytes) to target microorganisms for phagocytosis, by recognizing opsonins (for example antibodies or complement proteins) attached to the surface of the microorganism.

ORF (Open Reading Frame):

A series of nucleotide triplets (codons) coding for amino acids without any termination codons. These sequences are usually translatable into a peptide. In some examples an open reading frame encodes an antibody or antibody fragment, such as those disclosed herein.

Polypeptide:

A polymer in which the monomers are amino acid residues that are joined together through amide bonds, for example γ amide bonds (for example from the γ position of a glutamic acid side chain) or α amide bonds. When the amino acids are alpha-amino acids, either the L-optical isomer or the D-optical isomer can be used, for example D-glutamic acid to form poly-γ-D-glutamic acid (γDPGA). The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell.

Pharmaceutically Acceptable Carriers:

The pharmaceutically acceptable carriers useful in conjunction with the antibodies and fragments thereof disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of the antibodies and antibody fragments herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical or Therapeutic Agent:

A composition capable of inducing a desired therapeutic or prophylactic effect when properly administered to a subject or a cell. In some embodiments, a pharmaceutical or therapeutic agent is an antibody, or fragment thereof disclosed herein. In one specific non-limiting example, a pharmaceutical agent is an antibody that specifically binds *B. anthracis*.

Poly-γ-D-glutamic acid (γDPGA):

A homopolymer of glutamic acid residues linked by γ peptide bonds. The glutamic acid residues constituting the homopolymer are be solely in the D-form (γDPGA).

Purified:

The term purified does not require absolute purity; rather, it is intended as a relative term. Thus, for example, a purified peptide preparation is one in which the peptide or protein is more enriched than the peptide or protein is in its natural environment. In one embodiment, a preparation is purified such that the protein or peptide represents at least 50% of the total peptide or protein content of the preparation.

Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components. The disclosed antibodies or fragments thereof that specifically bind *B. anthracis* capsule, can be purified by any of the means known in the art. See for example *Guide to Protein Purification*, ed. Deutscher, Meth. Enzymol. 185, Academic Press, San Diego, 1990; and Scopes, *Protein Purification: Principles and Practice*, Springer Verlag, New York, 1982.

Recombinant:

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. Similarly, a recombinant protein is one encoded for by a recombinant nucleic acid molecule.

Sequence Identity:

The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a 4C or 11D antibody, the consensus anti-γDPGA chimpanzee monoclonal antibody, humanized form thereof, or chimeric form thereof, or functional fragment thereof will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds *Bacillus anthracis* capsule are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific Binding Agent:

An agent that binds substantially only to a defined target. In several embodiments, a specific binding agent is the monoclonal 4C or 11D antibody, the consensus anti-γDPGA chimpanzee monoclonal antibody humanized form thereof, chimeric form thereof, or functional fragment thereof. The term "specifically binds" refers to the preferential association of an antibody or other ligand, in whole or part, with that antigen or cells bearing that antigen, and not to other antigens or cells or tissues lacking that antigen. It is, of course, recognized that a certain degree of non-specific interaction may occur between a molecule and a non-target cell. Nevertheless, specific binding may be distinguished as mediated through specific recognition of the antigen. Although selectively reactive antibodies bind antigen, they may do so with low affinity. On the other hand, specific binding results in a much stronger association between the antibody or other specific binding agent and the antigen or cells bearing the antigen, than between the bound antibody (or other specific binding agent) and cells lacking the antigen. Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Transduced and Transformed:

A virus or vector "transduces" a cell when it transfers nucleic acid into the cell. A cell is "transformed" or "transfected" by a nucleic acid introduced into a cell when the DNA becomes stably replicated by the cell, either by incorporation of the nucleic acid into the cellular genome, or by episomal replication.

Numerous methods of transfection are known to those skilled in the art, such as: chemical methods (for example, calcium-phosphate transfection), physical methods (for example, electroporation, microinjection, particle bombardment), fusion (for example, liposomes), receptor-mediated endocytosis (for example, DNA-protein complexes, viral envelope/capsid-DNA complexes) and by biological infection by viruses such as recombinant viruses (see, for example, Wolff, J. A., ed, Gene Therapeutics, Birkhauser, Boston, USA (1994)). In the case of infection by retroviruses, the infecting retrovirus particles are absorbed by the target cells, resulting in reverse transcription of the retroviral RNA genome and integration of the resulting provirus into the cellular DNA.

Vector:

A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

II. Overview of Several Embodiments

B. anthracis is the causative agent of anthrax and is surrounded by a polypeptide capsule of poly-γ-D-glutamic acid (γDPGA). γDPGA is poorly immunogenic and has antiphagocytic properties. These properties of γDPGA reduce a body's ability to effectively fight B. anthracis infection using natural immunity. Thus, the need exists for therapeutic agents that prevent, treat, or reduce the effects of B. anthracis infection and/or to increase B. anthracis clearance from the body. Thus, this disclosure provides isolated monoclonal antibodies, chimeric forms of these antibodies, humanized forms of these antibodies and fragments thereof, that bind the capsule of B. anthracis. Methods of using the disclosed anti-γDPGA antibodies are also provided.

A Antibodies that Specifically Bind the Capsule of Bacillus Anthracis

Disclosed herein are anti-γDPGA monoclonal antibodies that specifically bind poly-γ-D-glutamic acid (γDPGA) on the capsule of B. anthracis, the causative agent of anthrax, but does not react with cells that do not express γDPGA on their surface. In particular embodiments, monoclonal antibodies directed against γDPGA are the anti-γDPGA chimpanzee monoclonal antibodies 4C and 11D, a consensus anti-γDPGA chimpanzee monoclonal antibody, chimeric forms thereof, humanized forms thereof, and fragments thereof, wherein any of these antibodies or fragments specifically bind γDPGA on the capsule of B. anthracis.

Generally, the monoclonal antibodies against γDPGA include a variable heavy ($V_H$) and a variable light ($V_L$) chain and specifically bind γDPGA on B. anthracis. The disclosed monoclonal antibodies, including chimeric forms thereof, humanized forms thereof, or fragments thereof, can specifically bind B. anthracis cells, and can bind the γDPGA antigen of such cells with an affinity constant (Kd) of at least $10^{-6}$ M, such as at least $10^{-7}$ M, at least $10^{-8}$ M, at least $10^{-9}$ M, at least $10^{-10}$ M, or at least $10^{-11}$ M. In specific embodiments, the 4C antibody can specifically bind B. anthracis cells, and can bind the γDPGA antigen of such cells with an affinity constant of $5.5 \times 10^{-10}$ M. In other embodiments, the 11D antibody can specifically bind B. anthracis cells, and can bind the γDPGA antigen of such cells with an affinity constant of $8.2 \times 10^{-11}$ M. In yet other embodiments, a consensus anti-γDPGA chimpanzee monoclonal antibody can specifically bind B. anthracis cells, and can bind the γDPGA antigen of such cells with an affinity constant of at least $10^{-6}$ M, such as at least $10^{-7}$ M, at least $10^{-8}$ M, at least $10^{-9}$ M, at least $10^{-10}$ M, or at least $10^{-11}$ M.

A consensus anti-γDPGA monoclonal antibody has a consensus light chain amino acid sequence and a consensus heavy chain amino acid sequence, wherein each consensus amino acid sequence represents the results of multiple sequence alignments of related sequences and the consensus sequence shows amino acid residues that are common among the aligned sequences. Common residues in the consensus light chain and heavy chain sequences are conserved amino acids and are generally important for antigen binding. The residues that vary among the aligned sequences represent amino acid positions that can tolerate sequence variability and are generally not important for antigen binding. In some embodiments of a consensus anti-γDPGA monoclonal antibody, at least one residue position within the light chain and/or heavy chain consensus amino acid sequences is represented by more than one amino acid. In other embodiments of a consensus anti-γDPGA monoclonal antibody, at least two, at least three, at least four, at least five, at least six, at least seven, at least eight, at least nine, at least ten, or more residue positions within the light chain and/or heavy chain consensus amino acid sequences is represented by more than one amino acid.

FIG. 1A and FIG. 1B show the amino acid sequence alignments of the anti-γDPGA antibodies 4C and 11D heavy chain and light chain, respectively. The alignments demonstrate the residues in the CDRs that are conserved between the 4C and 11D monoclonal antibodies. This alignment also shows positions that are not conserved between the antibodies, for example the first residue of the $V_H$-CDR1 can be either a valine (V) or a threonine (T). From this alignment a consensus sequence of the heavy chain (SEQ ID NO. 1) and light chain (SEQ ID NO. 2) anti-γDPGA antibody is constructed (the consensus anti-γDPGA chimpanzee monoclonal antibody). Thus, disclosed herein is a consensus anti-γDPGA chimpanzee monoclonal antibody. In some embodiments the consensus anti-γDPGA antibody has a antibody heavy chain variable domain amino acid sequence according to SEQ ID NO: 1. In some embodiments the consensus anti-γDPGA antibody has a antibody light chain variable domain amino acid sequence according to SEQ ID NO: 2.

In several non-limiting examples, the disclosed monoclonal antibody includes at least one of the variable domain light chain and/or at least one of the variable domain heavy chain amino acid sequences disclosed herein:

Consensus anti-γDPGA antibody heavy chain variable domain amino acid sequence:

(SEQ ID NO: 1)
LEX$_1$SGGGLVKPGX$_2$SLX$_3$LSCAASGFTFSX$_4$YAMHWVRQAPEKGLEWV

STIGX$_5$X$_6$GX$_7$TX$_8$X$_9$SDSVKGRX$_{10}$X$_{11}$IX$_{12}$RDNSX$_{13}$NTLX$_{14}$LQM

NSLRAEDTAVYYCX$_{15}$RX$_{16}$GYCSSTX$_{17}$CX$_{18}$SX$_{19}$X$_{20}$X$_{21}$FDX$_{22}$W

GQGTX$_{23}$VTVS, wherein $X_1$ can be E or no amino acid; $X_2$ can be D or G; $X_3$ can be R or T; $X_4$ can be V or T; $X_5$ can be A or R; $X_6$ can be G or S; $X_7$ can be N or D; $X_8$ can be W or L; $X_9$ can be H or Y; $X_{10}$ can be Y or F; $X_{11}$ can be T or S; $X_{12}$ can be A or S; $X_{13}$ can be Q or K; $X_{14}$ can be S or Y; $X_{15}$ can be V or A; $X_{16}$ can be R or K; $X_{17}$ can be R or N; $X_{18}$ can be D or Q; $X_{19}$ can be N or Q; $X_{20}$ can be D or Y; $X_{21}$ can be A or Y; $X_{22}$ can be I or Y; or $X_{23}$ can be M or L.

Consensus anti-γDPGA antibody light chain variable domain amino acid sequence: $X_1X_2X_3$TQSPSSLSA SVGX$_4$RVX$_5$ITCRASQDX$_6$NX$_7$X$_8$LAWX$_9$QQKPGKAPK X$_{10}$ LIX$_{11}$X$_{12}$X$_{13}$SSLQGGVX$_{14}$SRFSGSGSGTX$_{15}$ FTLTIS X$_{16}$LX$_{17}$PEDFATYYCX$_{18}$Q X$_{19}$X$_{20}$X$_{21}$ YPX$_{22}$TFGX$_{23}$GTKX$_{24}$EIX$_{25}$RT (SEQ ID NO: 2), wherein $X_1$ can be A or no amino acid; $X_2$ can be P or E; $X_3$ can be M or L; $X_4$ can be D or G; $X_5$ can be S or T; $X_6$ can be I or V; $X_7$ can be D or T; $X_8$ can be F or W; $X_9$ can be F or Y; $X_{10}$ can be R or P; $X_{11}$ can be F or Y; $X_{12}$ can be R or A; $X_{13}$ can be T or A; $X_{14}$ can be S or P; $X_{15}$ can be E or D; $X_{16}$ can be N or S; $X_{17}$ can be R or Q; $X_{18}$ can be L or Q; $X_{19}$ can be H or Y; $X_{20}$ can be S or K; $X_{21}$ can be S or H; $X_{22}$ can be P or L; $X_{23}$ can be Q or G; $X_{24}$ can be L or V or $X_{25}$ can be S or K.

Exemplary anti-γDPGA antibody 4C heavy chain variable domain amino acid sequence:

(SEQ ID NO: 3)
LEESGGGLVKPGDSLRLSCAASGFTFSVYAMHWVRQAPEKGLEWVSTIG

AGGNTWHSDSVKGRYTIARDNSQNTLSLQMNSLRAEDTAVYYCVRRGYC

SSTRCDSNDAFDIWGQGTMVTVS.

Exemplary anti-γDPGA antibody 4C light chain variable domain amino acid sequence:

(SEQ ID NO: 4)
APMTQSPSSLSASVGDRVSITCRASQDINDFLAWFQQKPGKAPKRLIFR

TSSLQGGVSSRFSGSGSGTEFTLTISNLRPEDFATYYCLQHSSYPPTFG

QGTKLEISRT.

Exemplary anti-γDPGA antibody 11D heavy chain variable domain amino acid sequence:

(SEQ ID NO: 5)
LESGGGLVKPGGSLTLSCAASGFTFSTYAMHWVRQAPEKGLEWVSTIGR

SGDTLYSDSVKGRFSISRDNSKNTLYLQMNSLRAEDTAVYYCARKGYCS

STNCQSQYYFDYWGQGTLVTVS

Exemplary anti-γDPGA antibody 11D light chain variable domain amino acid sequence:

(SEQ ID NO: 6)
ELTQSPSSLSASVGGRVTITCRASQDVNTWLAWYQQKPGKAPKPLIYAA

SSLQGGVPSRFSGSGSGTDFTLTISSLQPEDFATYYCQQYKHYPLTFGG

GTKVEIKRT.

In several embodiments, the antibody includes a $V_H$ polypeptide having an amino acid sequence at least about 90% identical, such as at least about 95% identical, at least about 98% identical, at least about 99% identical or even 100% identical, to the amino acid sequence set forth as SEQ ID NO: 1, SEQ ID NO: 3 or SEQ ID NO: 5 and a $V_L$ polypeptide having an amino acid sequence at least about 90% identical, such as at least about 95% identical, at least about 98% identical, at least about 99% identical or even 100% identical, to the amino acid sequence set forth as SEQ ID NO: 2, SEQ ID NO: 4, or SEQ ID NO: 6.

The production of chimeric antibodies (an antibody with non-human variable regions and human constant regions) and humanized antibodies (an antibody with non-human SDRs and/or CDRs and human framework regions) is well known in the art. Thus chimeric antibodies and humanized antibodies that specifically bind B. anthracis are disclosed.

In some embodiments, a chimeric antibody that specifically binds γDPGA on B. anthracis is a chimeric form of the 4C or 11D monoclonal antibody, the consensus anti-γDPGA chimpanzee monoclonal antibody, or a functional fragment thereof. In particular, non-limiting examples of a chimeric antibody, the antibody (or antibody fragment) can be an immunoglobulin having variable light chain and heavy chain regions from a donor monoclonal antibody (such as 4C or 11D or the consensus anti-γDPGA antibody, see Table 1) that binds B. anthracis, and heavy and light constant regions from a human acceptor immunoglobulin. Generally, the chimeric antibody specifically binds to B. anthracis and the γDPGA on such cells with an affinity constant of at most $10^{-11}$ M, such as at least $10^{-6}$ M, such as at least $10^{-7}$ M, at least $10^{-8}$ M, at least $10^{-9}$ M, at least $10^{-10}$ M, or at least $10^{-11}$ M.

In other embodiments, a humanized antibody that specifically binds B. anthracis is a humanized form of the 4C or 11D monoclonal antibody, the consensus anti-γDPGA chimpanzee monoclonal antibody, or a functional fragment thereof. In particular, non-limiting examples of the humanized antibody, the antibody (or antibody fragment) can be an immunoglobulin having complementarity determining regions (CDRs) from a donor monoclonal antibody (such as 4C or 11D or the consensus anti-γDPGA antibody, see Table 1) that binds B. anthracis, and heavy chain and light chain variable region frameworks from the same or different human acceptor immunoglobulins. Generally, the humanized antibody specifically binds to B. anthracis with an affinity constant of at most $10^{-11}$ M, such as at least $10^{-6}$ M, such as at least $10^{-7}$ M, at least $10^{-8}$ M, at least $10^{-9}$ M, at least $10^{-10}$ M, or at least $10^{-11}$ M. The location of the CDRs within the variable light chain and variable heavy chain amino acid sequences for the consensus anti-γDPGA chimpanzee monoclonal antibody, and for the 4C and 11D antibodies, are set forth in Table 1 below:

TABLE 1

| Antibody | chain | Sequence |
|---|---|---|
| Consensus | $V_H$-CDR1 | Amino acid 28-32 of SEQ ID NO: 1 |
| Consensus | $V_H$-CDR2 | Amino acid 47-55 of SEQ ID NO: 1 |
| Consensus | $V_H$-CDR3 | Amino acid 95-111 of SEQ ID NO: 1 |
| Consensus | $V_L$-CDR1 | Amino acid 23-33 of SEQ ID NO: 2 |
| Consensus | $V_L$-CDR2 | Amino acid 48-55 of SEQ ID NO: 2 |
| Consensus | $V_L$-CDR3 | Amino acid 88-96 of SEQ ID NO: 2 |
| 4C | $V_H$-CDR1 | Amino acid 28-32 of SEQ ID NO: 3 |
| 4C | $V_H$-CDR2 | Amino acid 47-55 of SEQ ID NO: 3 |
| 4C | $V_H$-CDR3 | Amino acid 95-111 of SEQ ID NO: 3 |
| 4C | $V_L$-CDR1 | Amino acid 23-33 of SEQ ID NO: 4 |
| 4C | $V_L$-CDR2 | Amino acid 48-55 of SEQ ID NO: 4 |
| 4C | $V_L$-CDR3 | Amino acid 88-96 of SEQ ID NO: 4 |
| 11D | $V_H$-CDR1 | Amino acid 27-31 of SEQ ID NO: 5 |
| 11D | $V_H$-CDR2 | Amino acid 46-54 of SEQ ID NO: 5 |
| 11D | $V_H$-CDR3 | Amino acid 94-11- of SEQ ID NO: 5 |
| 11D | $V_L$-CDR1 | Amino acid 22-32 of SEQ ID NO: 6 |
| 11D | $V_L$-CDR2 | Amino acid 47-54 of SEQ ID NO: 6 |
| 11D | $V_L$-CDR3 | Amino acid 87 to 95 of SEQ ID NO: 6 |

In some embodiments, a humanized antibody includes one or more CDRs from the variable region of the heavy chain of the consensus anti-γDPGA chimpanzee monoclonal antibody. Thus in some embodiments a humanized antibody includes amino acids 28-32 of SEQ ID NO: 1 (HCDR1), amino acids 47-55 of SEQ ID NO: 1 (HCDR2), or amino acids 95-111 of SEQ ID NO: 1 (HCDR3), wherein $X_4$ is V or T; $X_5$ is A or R; $X_6$ is G or S; $X_7$ is N or D; $X_8$ is W or L; $X_{16}$ is R or K; $X_{17}$ is R or N; $X_{18}$ is D or Q; $X_{10}$ is N or Q; $X_{20}$ is D or Y; $X_{21}$ is A or Y; or $X_{22}$ is I or Y. The antibody specifically binds γDPGA.

In other embodiments, a humanized antibody includes the CDRs from the variable region of the light chain of the consensus anti-γDPGA chimpanzee monoclonal antibody. Thus in some embodiments a humanized antibody includes amino acids 23-33 of SEQ ID NO: 2 (LCDR1), amino acids 48-55 of SEQ ID NO: 2 (LCDR2), or amino acids 88-96 of SEQ ID NO: 2 (LCDR3), wherein $X_4$ is V or T; $X_5$ is A or R; $X_6$ is G or S; $X_7$ is N or D; $X_8$ is W or L; $X_{16}$ is R or K; $X_{17}$ is R or N; $X_{18}$ is D or Q; $X_{19}$ is N or Q; $X_{20}$ is D or Y; $X_{21}$ is A or Y; and $X_{22}$ is I or Y; wherein $X_6$ is I or V; $X_7$ is D or T; $X_8$ is F or W; $X_{11}$ is F or Y; $X_{12}$ is R or A; $X_{13}$ is T or A; $X_{18}$ is L or Q; $X_{19}$ is H or Y; $X_{20}$ is S or K; $X_{21}$ is S or H; or $X_{22}$ is P or L.

In particular embodiments, a humanized antibody includes the CDRs from the variable region of the heavy chain of the chimpanzee monoclonal antibody 4C. Thus, in some embodiments, a humanized antibody includes amino acids 28-32 of SEQ ID NO: 3 (HCDR1), amino acids 47-55 of SEQ ID NO: 3 (HCDR2), or amino acids 95-111 of SEQ ID NO: 3 (HCDR3). In certain embodiments, a humanized antibody includes the CDRs from the variable region of the light chain of the chimpanzee monoclonal antibody 4C. Thus, in some embodiments, a humanized antibody includes amino acids 23-33 of SEQ ID NO: 4 (LCDR1), amino acids 48-55 of SEQ ID NO: 4 (LCDR2), or amino acids 88-96 of SEQ ID NO: 4 (LCDR3).

In some embodiments, a humanized antibody includes the CDRs from the variable region of the heavy chain of the chimpanzee monoclonal antibody 11D. Thus, in some embodiments, a chimeric antibody includes amino acids 27-31 of SEQ ID NO: 5 (HCDR1), amino acids 46-54 of SEQ ID NO: 5 (HCDR2), or amino acids 94-110 of SEQ ID NO: 5 (HCDR3). In other embodiments, a humanized antibody includes the CDRs from the variable region of the light chain of the chimpanzee monoclonal antibody 11D. Thus, in particular embodiments, a humanized antibody includes amino acids 22-32 of SEQ ID NO: 6 (LCDR1), amino acids 47-54 of SEQ ID NO: 6 (LCDR2), or amino acids 87-95 of SEQ ID NO: 6 (LCDR3).

Humanized monoclonal antibodies can be produced by transferring donor CDRs from heavy and light variable chains of the donor chimpanzee immunoglobulin (such as the consensus anti-γDPGA chimpanzee monoclonal antibody, the chimpanzee monoclonal antibody 4C, or the chimpanzee monoclonal antibody 11D) into a human framework region. In some embodiments, human residues in the framework regions are substituted with residues from the donor antibody, if required to retain affinity. Techniques for producing humanized monoclonal antibodies are described, for example, by Jones et al., *Nature* 321:522, 1986; Riechmann et al., *Nature* 332:323, 1988; Verhoeyen et al., *Science* 239: 1534, 1988; Carter et al., *Proc. Nat'l Acad. Sci. U.S.A.* 89:4285, 1992; Sandhu, *Crit. Rev. Biotech.* 12:437, 1992; and Singer et al., *J. Immunol.* 150:2844, 1993. The antibody may be of any isotype, for example, IgA, IgD, IgE, IgG, or IgM. Specific non-limiting examples of subclass of an IgG antibody include $IgG_1$, $IgG_2$, $IgG_3$, or $IgG_4$.

In one embodiment, the sequence of the humanized immunoglobulin heavy chain variable region framework can be at least about 65% identical to the sequence of the donor immunoglobulin heavy chain variable region framework. In other embodiments, the sequence of the humanized immunoglobulin heavy chain variable region framework can be at least about 75%, at least about 85%, at least about 95%, at least about 98%, or at least about 99% identical to the sequence of the donor immunoglobulin heavy chain variable region framework. The sequences of the heavy and light chain frameworks are known in the art. Human framework regions, and mutations that can be made in a humanized antibody framework regions, are known in the art (see, for example, in U.S. Pat. No. 5,585,089, which is incorporated herein by reference).

Exemplary human antibodies LEN and 21/28'CL are of use in providing framework regions. Exemplary light chain frameworks of human monoclonal antibody LEN have the following sequences:

```
                                       (SEQ ID NO: 11)
FR1: DIVMTQS PDSLAVSLGERATINC (SEQ ID NO: 12)
FR2: WYQQKPGQPPLLIY (SEQ ID NO: 13)
FR3: GVPDRPFGSGSGTDFTLTISSLQAEDVAVYYC (SEQ ID NO: 14)
FR4: FGQGQTKLEIK
```

Exemplary heavy chain frameworks of human monoclonal antibody 21/28'CL have the following sequences:

```
                                       (SEQ ID NO: 15)
FR1: QVQLVQSGAEVKKPQASVKVSCKASQYTFT (SEQ ID NO: 16)
FR2: WVRQAPGQRLEWMG (SEQ ID NO: 17)
FR3: RVTITRDTSASTAYMELSSLRSEDTAVYYCAR (SEQ ID NO: 18)
FR4: WGQGTLVTVSS.
```

The disclosed antibodies can be of any isotype. The monoclonal antibody can be, for example, an IgM or an IgG antibody, such as $IgG_1$ or an $IgG_2$. In one embodiment, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a light chain constant region ($C_L$) or heavy chain constant region ($C_H$) from a different isotype or class of immunoglobulin molecule. This can be achieved using a vector or nucleic acid molecule that comprises a $C_L$ or $C_H$ chain. Nucleic acid molecules encoding such sequences are known in the art. In some examples, the regions of an antibody that determine the antibody isotype or class can be substituted with the corresponding region of another antibody isotype or class using recombinant methods. For example, an antibody that specifically binds *B. anthracis* that is an IgM may be switched to an IgG. In particular, non-limiting examples, class switching can be used to convert one IgG subclass to another, such as from $IgG_1$ to $IgG_2$, $IgG_3$, or $IgG_4$. In other embodiments, an IgG constant region can be added to an antibody fragment having the antigen binding domains, such as a Fab fragment. In a specific non-limiting example, a constant region from a human IgG1 (human γ1 constant region) is combined with a chimpanzee Fab region.

Antibody fragments, such as Fab, F(ab')$_2$, and Fv which include a heavy chain and light chain variable region and are capable of binding the epitopic determinant on *B. anthracis*, are encompassed by the present disclosure. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of an scFV. This has also been termed a "miniantibody."

Methods of making these fragments are known in the art (see for example, Harlow and Lane, *Antibodies: A Laboratory Manual*, Cold Spring Harbor Laboratory, New York, 1988). Antibodies, such as chimpanzee monoclonal antibodies, chimeric antibodies, and humanized antibodies, include full length molecules as well as fragments thereof, such as Fab, F(ab')$_2$, and Fv which include a heavy chain and light chain variable region and are capable of binding the epitopic determinant. In some embodiments, the antibodies have V$_L$ (for example, SEQ ID NO: 2, SEQ ID NO: 4; or SEQ ID NO: 6) and V$_H$ (for example, SEQ ID NO: 1, SEQ ID NO: 3; or SEQ ID NO: 5) regions, or portions thereof, such as the CDRs or SDRs. Fv antibodies are typically about 25 kDa and contain a complete antigen-binding site with three CDRs per each heavy chain and each light chain. To produce these antibodies, the V$_H$ and the V$_L$ can be expressed from two individual nucleic acid constructs in a host cell. If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise V$_H$ and V$_L$ chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; and Pack et al., *Bio/Technology* 11:1271, 1993).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules Amino acid substitutions (such as at most one, at most two, at most three, at most four, or at most five amino acid substitutions) can be made in the V$_H$ and the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, one of skill in the art can readily review SEQ ID NOs: 1-6 locate one or more of the amino acids in the brief table above, identify a conservative substitution, and produce the conservative variant using well-known molecular biology techniques. Generally, conservative variants will bind the target antigen with an equal to or greater efficiency than the parent monoclonal antibody.

Monoclonal antibodies may be produced to either the normal γDPGA protein or mutant forms of this protein. In one embodiment, monoclonal antibodies to γDPGA can be prepared by hybridoma fusion. A monoclonal antibody to epitopes of γDPGA, identified and isolated as described, can be prepared from murine hybridomas according to the classical method of Kohler and Milstein (Nature 256:495-497, 1975) or derivative methods thereof. In one specific, non-limiting embodiment, a mouse is repetitively inoculated with a few micrograms of the selected protein over a period of a few weeks. The mouse is then sacrificed, and the antibody-producing cells of the spleen isolated. The spleen cells are fused with mouse myeloma cells using polyethylene glycol, and the excess, non-fused, cells destroyed by growth of the system on selective media comprising aminopterin (HAT media). Successfully fused cells are diluted and aliquots of the dilution placed in wells of a microtiter plate, where growth of the culture is continued. Antibody-producing clones are identified by detection of antibody in the supernatant fluid of the wells by immunoassay procedures, such as ELISA, as originally described by Engvall (*Enzymol.* 70(A):419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988). Hybridoma cells, and their progeny, that secrete monoclonal antibodies are also encompassed by this disclosure.

In another embodiment, recombinant methods are used to prepare monoclonal antibodies against γDPGA. In one specific, non-limiting example to obtain therapeutically useful anti-γDPGA monoclonal antibodies, a host, such as a chimpanzee, can be immunized with conjugates of a 10 or 15-mer of D-glutamic acid polymers (γDPGA) bound to an immunogenic carrier protein such as recombinant protective antigen (rPA) or tetanus toxoid (TT). After several immunizations, the host develops strong immune responses to γDPGA. A combinatorial Fab library of mRNA derived from the host's bone marrow can be prepared and distinct clones expressing Fabs reactive with native γDPGA recovered. Fabs can be converted into full-length IgG with human γ1 heavy chain constant regions. Such monoclonal antibodies can be tested for opsonophagocytic killing of bacilli in an in vitro assay. As chimpanzee immunoglobulins are virtually identical to human immunoglobulins, these chimpanzee anti-γDPGA monoclonal antibodies have clinically useful applications.

Effector molecules, such as therapeutic, diagnostic, or detection moieties can be linked to an antibody that specifically binds γDPGA on $B.$ $anthracis$, using any number of means known to those of skill in the art. Both covalent and noncovalent attachment means may be used. The procedure for attaching an effector molecule to an antibody varies according to the chemical structure of the effector. Polypeptides typically contain a variety of functional groups (such as carboxylic acid (COOH), free amine ($-NH_2$) or sulfhydryl ($-SH$) groups) which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company (Rockford, Ill.). The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (for example when exposed to tumor-associated enzymes or acidic pH) may be used.

In view of the large number of methods that have been reported for attaching a variety of radiodiagnostic compounds, radiotherapeutic compounds, label (such as enzymes or fluorescent molecules), and other agents to antibodies, one skilled in the art will be able to determine a suitable method for attaching a given agent to an antibody or other polypeptide. In some examples a label is a detectable label such as a fluorophore (for example FTIC, PE and the like), an enzyme (for example HRP), a radiolabel, or a nanoparticle (for example a gold particle or a semiconductor nanocrystal, such as a quantum dot (QDOT®)).

The antibodies or antibody fragments disclosed herein can be derivatized or linked to another molecule (such as another peptide or protein). In general, the antibodies or portion thereof is derivatized such that the binding to γDPGA on $B.$ $anthracis$ is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody that specifically binds γDPGA on $B.$ $anthracis$ can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect $Bacillus$ $anthracis$ by x-ray, emission spectra, or other diagnostic techniques. Examples of labels for polypeptides include, but are not limited to, the following radioisotopes or radionuclides: $^{3}H$, $^{14}C$, $^{15}N$, $^{35}S$, $^{90}Y$, $^{99}Tc$, $^{111}In$, $^{125}I$, $^{131}I$.

Nucleic acids encoding the amino acid sequences of the antibodies that bind γDPGA on *B. anthracis* are also provided herein. Exemplary nucleic acid sequences are as follows:

Anti-γDPGA 4C heavy chain variable domain DNA sequence:

(SEQ ID: 7)
```
ctcgaggagtctgggggaggcctggtaaagcctggggattccctgagac
tctcgtgtgcagcctctggattcaccttcagtgtctatgctatgcactg
ggtccgccaggctccagagaaggggctggagtgggtctcaactattggt
gctggtggtaatacgtggcactccgactctgtcaagggccgatacacca
ttgccagagacaattcccagaatacgctgtctctgcaaatgaacagcct
gagagccgaggacacggccgtgtattactgtgtgagaaggggatactgt
agcagtactaggtgcgacagtaatgatgcttttgatatctggggccaag
ggacaatggtcaccgtctct
```

Anti-γDPGA 4C light chain variable domain DNA sequence:

(SEQ ID: 8)
```
gctccgatgacccagtctccatcctcattgtctgcatctgtgggagaca
gagtcagcatcacttgtcgggcgagtcaggacattaacgattttttggc
ctggtttcagcagaaaccagggaaagcccctaagcgtctgatctttcgt
acttccagtttgcaaggtggagtctcatcaagattcagtggcagtggat
ctgggacagaattcactctcacaatcagcaacctgcggcctgaagattt
tgcaacttattactgtctgcagcatagttcttaccctccgaccttcggc
caagggaccaaactggagatcagccgaact
```

Anti-γDPGA 11D heavy chain variable domain DNA sequence:

(SEQ ID: 9)
```
ctcgagtctgggggaggcttggtcaagccgggggggtccctgacactct
cgtgtgcagcctctggattcaccttcagtacctatgctatgcactgggt
ccgccaggctccagagaaggggctggagtgggtctcaactattggtcgt
agtggtgacacgttgtactcagactctgtcaagggccgattcagcatct
ccagagacaattccaagaacaccctgtatctgcaaatgaacagcctgag
agccgaggacacggccgtgtattattgtgcgagaaagggatattgtagt
agtaccaactgtcagtcccaatattactttgactactggggccagggaa
ccctggtcaccgtctcc
```

Anti-γDPGA 11D light chain variable domain DNA sequence:

(SEQ ID: 10)
```
gagctcacccagtctccatcctcactgtctgcatctgtgggaggcagag
tcaccatcacttgtcgggccagtcaggatgttaacacctggttagcctg
gtatcagcagaaaccagggaaagcccctaagcccctgatctatgctgca
tccagtttgcaaggtggggtcccatcaaggtttagcggcagtgggtctg
ggacagatttcactctaaccatcagcagcctgcagcctgaagattttgc
``` aacttattactgccaacaatataaacattaccctctcactttcggtgga gggaccaaggtggagatcaaacgaact

Nucleotides molecules encoding the antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode one antibody sequence. Thus, nucleic acids encoding antibodies, conjugates and fusion proteins are provided herein. Nucleic acid molecules encoding the 4C and 11D Fab sequences were deposited with the ATCC on Nov. 14, 2008, in accordance with the Budapest Treaty (Accession Nos. PTA-9610 and PTA-9609, respectively).

Nucleic acid sequences encoding the human antibodies that specifically bind γDPGA on *B. anthracis* can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding a human antibody that specifically binds γDPGA on *B. anthracis* can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill in the art.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody of use is prepared by inserting the cDNA which encodes a variable region from an antibody into a vector which comprises the cDNA encoding an effector molecule (EM), such as an enzyme or label. The insertion is made so that the variable region and the EM are read in frame so that one continuous polypeptide is produced. Thus, the encoded polypeptide contains a functional Fv region and a functional EM region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody, so that the enzyme or polypeptide marker is located at the carboxyl terminus of the heavy chain variable region. The heavy chain-variable region can subsequently be ligated to a light chain variable region of the antibody using disulfide bonds. In a yet another example, cDNA encoding an enzyme or a polypeptide marker is ligated to a light chain variable region of an antibody, so that the enzyme or polypeptide marker is located at the carboxyl terminus of the light chain variable region. The light chain-variable region can subsequently be ligated to a heavy chain variable region of the antibody using disulfide bonds.

Once the nucleic acids encoding the antibody, labeled antibody, or fragment thereof are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

Polynucleotide sequences encoding the antibody, labeled antibody, or functional fragment thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, labeled antibody, or functional fragment thereof can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect, and mammalian organisms. Methods of expressing DNA sequences having eukaryotic or viral sequences in prokaryotes are well known in the art. Biologically functional viral and plasmid DNA vectors capable of expression and replication in a host are known in the art. Nucleic acid molecules encoding the 4C and 11D Fab sequences were deposited with the ATCC on Nov. 14, 2008, in accordance with the Budapest Treaty (Accession Nos. PTA-9610 and PTA-9609, respectively). In one specific, non-limiting example, an expression vector encoding the 4C Fab sequence is pComb3H-4C, deposited with the ATCC on Nov. 14, 2008, in accordance with the Budapest Treaty (Accession No. PTA-9610). In another specific, non-limiting example, an expression vector encoding the 11D Fab sequence is pComb3H-11D, deposited with the ATCC on Nov. 14, 2008, in accordance with the Budapest Treaty (Accession No. PTA-9609).

Transformation of a host cell with recombinant DNA may be carried out by conventional techniques, as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, methods of DNA transfection, such as calcium phosphate co-precipitation, conventional mechanical procedures such as microinjection, electroporation, insertion of a plasmid encased in liposomes, or virus vectors may be used. Eukaryotic cells can also be cotransformed with polynucleotide sequences encoding the disclosed antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the antibody, labeled antibody or functional fragment thereof can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90% to 95%, 95% to 98%, or 98% to 99% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology.* Vol. 2: *Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

B Therapeutic Compositions

Compositions, such as therapeutic or pharmaceutical compositions, are provided that include one or more of the disclosed anti-γDPGA antibodies, humanized forms thereof, chimeric forms thereof, or fragments thereof that specifically bind *B. anthracis*. The antibodies or fragments thereof can be administered in vitro, ex vivo, or in vivo to a cell or subject. It is desirable to prepare the antibodies or fragments thereof as a pharmaceutical composition appropriate for the intended application, for example to inhibit or treat a *B. anthracis* infection or for the detection of a *B. anthracis* infection. Accordingly, methods for making a medicament or pharmaceutical composition containing a disclosed anti-γDPGA antibody or fragment thereof, alone or in combination with other agents that inhibit, treat, or detect *B. anthracis* infection, are disclosed herein. In some embodiments, the disclosed anti-γDPGA antibodies or fragments thereof are administered with one or more isolated anti-*B. anthracis* (anti-anthrax) antibodies or fragment thereof, such as anti-anthrax toxin antibodies. In particular embodiments, anti-anthrax toxin antibodies include one or more of an anti-PA, -LF or -EF antibody or fragment thereof (for example, the anti-PA, -LF and -EF antibodies disclosed in International patent publication Nos. WO08103845 and WO07084107, both of which are incorporated herein by reference in their entirety) are included herein. Anti-γDPGA antibodies can be prepared for administration alone or with other agents, such as antibiotics (for example one or more isolated anti anthrax toxin antibodies or fragment thereof, such as one or more of an anti-PA, -LF or -EF antibody or fragment thereof) and/or other proteins, such as with complement protein or fragments thereof.

In some examples, a therapeutic composition includes a disclosed anti-γDPGA antibody. In other examples, a therapeutic composition includes one or more isolated anti-anthrax toxin antibodies or fragment thereof, such as one or more of an anti-PA, -LF and -EF antibody or fragment thereof. In yet other examples, a therapeutic composition includes a disclosed anti-DPGA antibody or a fragment thereof and one or more isolated anti anthrax toxin antibodies or a fragment thereof, such as one or more of an anti-PA, -LF and -EF antibody.

Typically, preparation of a pharmaceutical composition (for use as a medicament or in the manufacture of a medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow the disclosed anti-γDPGA antibody or fragment thereof to interact with *B. anthracis* cells that are in a subject.

Antibodies may be provided in lyophilized form and rehydrated with sterile water before administration, although they are also provided in sterile solutions of known concentration. In some examples, the antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Therapeutic compositions can be provided as parenteral compositions, such as for injection or infusion. Such compositions are formulated generally by mixing a disclosed anti-γDPGA antibody or fragment thereof and/or one or more isolated anti anthrax toxin antibodies or fragment thereof, such as one or more of an anti-PA, -LF and -EF antibody or fragment thereof, at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed anti-γDPGA antibody or fragment thereof and/or one or more isolated anti anthrax toxin antibodies or fragment thereof, such as one or more of an anti-PA, -LF and -EF antibody or fragment thereof, can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The disclosed anti-γDPGA antibody or fragment thereof, optionally together with excipients and/or one or more isolated anti anthrax toxin antibodies or fragment thereof, such as one or more of an anti-PA, -LF and -EF antibody or fragment thereof, can also be in the form of a lyophilisate and can be made into a solution prior to parenteral administration by the addition of suitable solvents.

Solutions such as those that are used, for example, for parenteral administration can also be used as infusion solutions.

Pharmaceutical compositions can include an effective amount (such as a therapeutically effective amount) of a disclosed anti-γDPGA antibody or fragment thereof, and/or one or more isolated anti-anthrax toxin antibodies or fragment thereof, such as one or more of an anti-PA, -LF or -EF antibody or fragment thereof in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 15th Edition (1975).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include a disclosed anti-γDPGA antibody or fragment thereof and/or one or more isolated anti-anthrax toxin antibodies or fragment thereof, such as one or more of an anti-PA, -LF or -EF antibody or fragment thereof in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

Additional formulations are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders. Exemplary formulations can be found in U.S. Patent publication No. 20020031527. When the route is topical, the form may be a cream, ointment, salve or spray.

Typical subjects intended for treatment with the pharmaceutical compositions and methods of the present disclosure include humans, as well as non-human primates and other animals. To identify subjects for prophylaxis or treatment according to the methods of the disclosure, accepted screening methods are employed to determine risk factors associated with a targeted or suspected disease or condition (for example, an infection associated with a particular pathogen of interest, such as *B. anthracis*) or to determine the status of an existing disease or condition in a subject. These screening methods include, for example, diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure.

C. Methods of Treatment

Methods of treating or inhibiting a *B. anthracis* infection in a subject are disclosed. Subjects that would benefit from such methods include for example, a subject that has a *B. anthracis* infection or is at risk of developing a *B. anthracis* infection, such as a subject that has been exposed or is believed to have been exposed to *B. anthracis*, for example a subject exposed or potentially exposed to *B. anthracis* spores. In particular examples, the method is used to enhance the opsonophagocytosis of *B. anthracis* in a subject who is infected with (or at risk of being infected with) *B. anthracis*. In some examples a subject is selected for treatment that has or is at risk for developing an infection by *B. anthracis*, for example a prophylactic administration. The methods include administering to the subject a therapeutically effective amount of one or more of the anti-γDPGA antibodies, or fragments thereof disclosed herein. In some examples, a subject is administered one or more of the 4C monoclonal antibody, the 11D monoclonal antibody, the consensus anti-γDPGA chimpanzee monoclonal antibody, a chimeric form thereof, or a humanized form thereof, or a fragment thereof.

Without being bound by theory, the anti-γDPGA monoclonal antibodies 4C and 11D can function as opsonophagocytic antibodies. Thus, in some embodiments, the administration of the 4C monoclonal antibody, the 11D monoclonal antibody, the consensus anti-γDPGA chimpanzee monoclonal antibody, a chimeric form thereof, or a humanized form thereof, or a fragment thereof enhances the ability of the subject's immune system (and specifically the ability of effector cells, such as macrophages, eosinophils, and neutrophils, of the subject) to opsonophagocytose *B. anthracis* as a result of the *B. anthracis* being specifically bound by the 4C monoclonal antibody, the 11D monoclonal antibody, the consensus anti-γDPGA chimpanzee monoclonal antibody, a chimeric form thereof, or a humanized form thereof, or a fragment thereof. Complement proteins and fragments thereof assist in opsonophagocytic killing of pathogens by binding to opsonic antibodies, such as the 4C monoclonal antibody or the 11D monoclonal antibody, and facilitating the opsonization by effector cells.

It is contemplated that the disclosed anti-γDPGA antibodies can work in conjunction with anti-anthrax toxin antibodies or fragment thereof to inhibit and/or treat infection by *B. anthracis*. Thus, in some examples, the subject is also administered a pharmaceutically effective amount of one or more isolated anti-anthrax toxin antibodies or fragment thereof, such as one or more of an anti-PA, -LF or -EF antibody or fragment thereof. Examples of anti-anthrax toxin antibodies or fragment thereof, such as anti-PA, -LF or -EF antibodies, can be found in International patent publication Nos. WO08103845 and WO07084107, both of which are incorporated herein by reference in their entirety. In some examples the disclosed anti-γDPGA antibodies are administered concurrently with one or more of isolated anti-anthrax toxin antibodies or fragment thereof, such as one or more of an anti-PA, -LF or -EF antibody or fragment thereof. In some example the disclosed anti-γDPGA antibodies are administered sequentially with one or more of isolated anti-anthrax toxin antibodies or fragment thereof, such as one or more of an anti-PA, -LF or -EF antibody or fragment thereof. Sequential administration can be separated by any amount of time so long as the desired effect are achieved, for example prevention or treatment of an anthrax infection. Multiple administrations of the compositions described herein are also contemplated.

Administration of therapeutic compositions can be by any common route as long as the target tissue is available via that route. This includes oral, nasal (such as intranasal), ocular, buccal, enteral, intravitral, or other mucosal (such as rectal or vaginal) or topical administration. Alternatively, administration will be by orthotopic, intradermal subcutaneous, intramuscular, parentral intraperitoneal, or intravenous injection routes. Such pharmaceutical compositions are usually administered as pharmaceutically acceptable compositions that include physiologically acceptable carriers, buffers or other excipients.

An effective amount of the pharmaceutical composition is determined based on the intended goal, for example to inhibit and/or treat a pathogenic infection of a human or non-human subject. The administration of the pharmaceutical compositions of the disclosure can be for either prophylactic or therapeutic purpose. When provided prophylactically, the pharmaceutical composition is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the pharmaceutical compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of a disclosed anti-γDPGA antibody or fragment thereof (for example, amounts that are effective to alleviate one or more symptoms of a *B. anthracis* infection).

The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes both a disclosed anti-γDPGA antibody or fragment thereof alone or in conjunction with one or more isolated anti anthrax toxin antibodies or fragment thereof or fragment thereof, such as one or more of an anti-PA, -LF and -EF antibody or fragment thereof, time and route of administration, other drugs or treatments being administered concurrently, as well as the specific pharmacology of the therapeutic compositions for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a disclosed anti-γDPGA antibody or fragment thereof and/or other biologically active agent within the methods and formulations of the disclosure is about 0.01 mg/kg body weight to about 100 mg/kg body weight, such as about 0.05 mg/kg to about 5 mg/kg body weight, or about 0.2 mg/kg to about 2 mg/kg body weight or greater.

Therapeutic compositions that include a disclosed therapeutic agent can be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414) Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions including a disclosed therapeutic agent are administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec,

*J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

The pharmaceutical compositions (medicaments) can be prepared for use in prophylactic regimens and administered to human or non-human subjects to protect against infection by *B. anthracis*. Thus, the pharmaceutical compositions typically contain a pharmaceutically effective amount of a disclosed anti-γDPGA antibody or fragment thereof and optionally a pharmaceutically effective amount of a complement protein or a fragment thereof. In some cases the compositions are administered following infection, for example to treat the infection an increase *B. anthracis* clearance, in such applications, the pharmaceutical composition is administered in a therapeutically effective amount. A therapeutically effective amount is a quantity of a composition used to achieve a desired effect in a subject. For instance, this can be the amount of the composition necessary to inhibit infection by *B. anthracis*, to increase *B. anthracis* clearance from the subject or to prevent or measurably alter outward symptoms of *B. anthracis* infection from a subject. When administered to a subject, a dosage will generally be used that will achieve target tissue concentrations that has been shown to achieve an in vitro or in vivo effect.

D. Diagnostic Methods and Kits

Methods are provided herein for the detection *B. anthracis* in vitro or in vivo for example in a biological sample obtained from a subject. In some examples, detecting the presence of *B. anthracis* in a sample indicates that the subject from which the sample was obtained has a *B. anthracis* infection. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a rat, mouse, cow, dog, guinea pig, rabbit, or primate. In some embodiments, the primate is macaque, chimpanzee, or a human.

In some examples, a sample is an environmental sample, such as a sample obtained by swabbing a surface. Detection of *B. anthracis* in an environmental sample indicates that the environment from witch the sample is obtained is contaminated with *B. anthracis*.

The disclosed method includes contacting a sample, such as biological sample or environmental sample, with one or more of the disclosed anti-γDPGA antibodies or fragments thereof under conditions conductive to the formation of an immune complex between the γDPGA present on the surface of *B. anthracis* and the anti-γDPGA antibodies or fragments thereof, and detecting the immune complex, to detect the *B. anthracis* the sample.

In one embodiment, a disclosed anti-γDPGA antibody or fragment thereof is directly labeled with a detectable label. In another embodiment, the disclosed anti-γDPGA antibody or fragment thereof (the first antibody) is unlabeled and a second antibody or other molecule that can bind the a disclosed anti-γDPGA antibody or fragment thereof is labeled. As is well known to one of skill in the art, a second antibody is chosen that is able to specifically bind the specific species and class of the first antibody. For example, if the first antibody is an IgG, then the secondary antibody may be an anti-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In other embodiments, *B. anthracis* is assayed in a sample by a competition immunoassay utilizing *B. anthracis* standards, such as γDPGA standards labeled with a detectable substance and a disclosed anti-γDPGA antibody or fragment thereof. In this assay, the sample, the labeled *B. anthracis* standards and the anti-DPGA antibody or fragment thereof are combined and the amount of labeled *B. anthracis* standard bound to the unlabeled antibody is determined. The amount of *B. anthracis* in the biological sample is inversely proportional to the amount of labeled *B. anthracis* standard bound to the anti-γDPGA antibody or fragment thereof.

The immunoassays and method disclosed herein can be used for a number of purposes. In one embodiment, a disclosed anti-γDPGA antibody or fragment thereof can be used to detect the amount of *B. anthracis* in a biological sample.

In some embodiments, a kit is provided for detecting *B. anthracis* in a sample, such as a biological sample or an environmental sample. Kits for detecting a *B. anthracis* will typically contain one or more of the disclosed anti-γDPGA antibodies or fragment thereof, such as any of the antibodies or fragments disclosed herein. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In some embodiments, a kit additionally includes instructional materials. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting

*B. anthracis* in a sample generally includes the steps of contacting the biological sample with an antibody which specifically reacts, under immunologically reactive conditions, to γDPGA on the surface of *B. anthracis*. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbant assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Thus, the disclosed antibodies or fragments thereof can be used in a conventional immunoassay, including, without limitation, an ELISA, an RIA, FACS, tissue immunohistochemistry, Western blot or immunoprecipitation.

EXAMPLES

Example 1

Isolation and Characterization of Poly-γ-D-glutamic acid Specific Fabs

Peptides (10 or 15 amino acids long) representing a fragment of poly-γ-D-glutamic acid (γDPGA) capsule of *B. anthracis* were conjugated to either *B. anthracis* recombinant protective antigen (rPA) or tetanus toxoid (TT) and the conjugates were used to immunize chimpanzees. Fab-encoding gene fragments were amplified from the cDNA of chimpanzee bone marrow-derived mononuclear cells and cloned into pComb3H vector. The Fab-displaying phage library was panned against PGA and specific phage clones were recovered. DNA sequencing of the variable regions of heavy (VH) and light (VL) chains from PGA-specific clones showed that there were two distinct clones. These two clones were designated 4C and 11D. The 4C and 11D VH and VL amino acid sequences are shown in FIGS. 1A and 1B.

The Fab sequences were converted into full-length IgG with human γ1 constant regions and the IgGs were examined for their binding specificity by ELISA. Two anti-γDPGA monoclonal antibodies are specific to γDPGA as the monoclonal antibodies bound to γDPGA, but not to unrelated proteins (BSA, thyroglobulin, phosphorylase b, lysozyme, and cytochrome-c) (FIG. 2).

Example 2

Binding Affinity

This example shows the affinity measurement of the disclosed monoclonal antibodies for γDPGA. The kinetic analysis of the anti-γDPGA mAb was performed in a BIAcore 1000 (GE healthcare, Piscataway, N.J.). 4C or 11D IgG was immobilized onto a CM5 chip using N-hydroxysuccinimide/1-ethyl-3-(3-dimethylaminopropyl)-carbodiimide coupling chemistry. Two-fold serial dilutions of synthetic 10-mer peptide of r-D-glutamic acids from 20 nM to 0.078 nM were injected onto the chip surface. The kinetic interaction between γDPGA peptide and 4C and 11D IgG was displayed in the sensorgram and evaluated by BIAevaluation software using 1:1 (Langmuir) binding model. The result showed that the two anti-γDPGA monoclonal antibodies had high affinities for the antigen (Table 2).

TABLE 2

Binding affinities of anti-γDPGA mAbs

| mAb | $K_{on}$ ($M^{-1}s^{-1}$) | $k_{off}$ ($s^{-1}$) | $K_d$ (nM) |
|---|---|---|---|
| 4C | $4.2 \times 10^6$ | $2.3 \times 10^{-3}$ | 0.55 |
| 11D | $1.1 \times 10^6$ | $9.04 \times 10^{-5}$ | 0.082 |

Example 3

Capsular Quellung Type Reaction

The capsular quellung type reaction was examined for the 4C monoclonal antibody. The Quellung reaction is a biochemical reaction in which antibodies bind to the capsule of *Streptococcus pneumoniae, Klebsiella pneumoniae, Neisseria meningitidis* and *Haemophilus influenzae* and thus allow them to be visualized under a microscope. If the reaction is positive, the capsule becomes opaque and appears to enlarge. Quellung is the German word for "swelling" and describes the microscopic appearance of pneumococcal or other bacterial capsules after their polysaccharide antigen has combined with a specific antibody. As a result of this combination, and precipitation of the large, complex molecule formed, the capsule appears to swell, because of increased surface tension, and its outlines become clearly demarcated.

Cells of formalin-killed *B. anthracis* (Ames 34 strain) were incubated with IgG1 of anti-γDPGA 4C monoclonal antibody at concentrations of 25 μg/ml, 50 μg/ml and 100 μg/ml. The Fab of anti-γDPGA or IgG1 of anti-PA at 100 μg/ml were used as controls. The reactions were assessed by DIC microscopy. The results (FIG. 3) showed that IgG1 of anti-γDPGA at concentrations of 50 μg/ml and 100 μg/ml produced a rim type reaction at the capsule perimeter. The reaction is specific for the anti-γDPGA monoclonal antibody since anti-PA IgG1 at 100 μg/ml did not produce a similar reaction. The reaction was also not observed when a lower concentration (25 μg/ml) of IgG1 or monovalent Fab of anti-γDPGA at a high concentration (100 μg/ml) was used.

Example 4

Opsonophagocytic Activity of Anti-γDPGA Monoclonal Antibodies

This example shows the measurement of opsonophagocytic activity of the 4C and 11D anti-γDPGA monoclonal antibodies. The opsonophagocytic activity of anti-γDPGA monoclonal antibodies was measured by their ability to kill *B. anthracis* cells in the presence of human polymorphonuclear leukocytes and complement. Opsonophagocytosis was defined as ≧50% killing compared with growth in control (no antibody) wells. The results showed that both anti-γDPGA mAbs had opsonophagocytic activity (FIG. 4).

Example 5

Protection of Mice Against Challenge with Virulent Anthrax Spores

This example shows that the 4C and 11D anti-DPGA monoclonal antibodies provide efficient protection of mice against challenge with virulent anthrax spores. IgG1(hG1) and IgG3 (hG3) isotypes for each of the 4C and 11D monoclonal antibodies were generated and the doses of 3 mg, 1 mg or 0.3 mg of the antibodies were administered intraperitoneally into BALB/c mice. Eight mice were used for each dose group. The mice were infected intra-tracheally with $1.48 \times 10^4$ *B. anthracis* (Ames strain) spores at approximately 18 hours post-monoclonal antibody treatment. The survival was monitored twice daily for 2 weeks post challenge.

Figure 5:
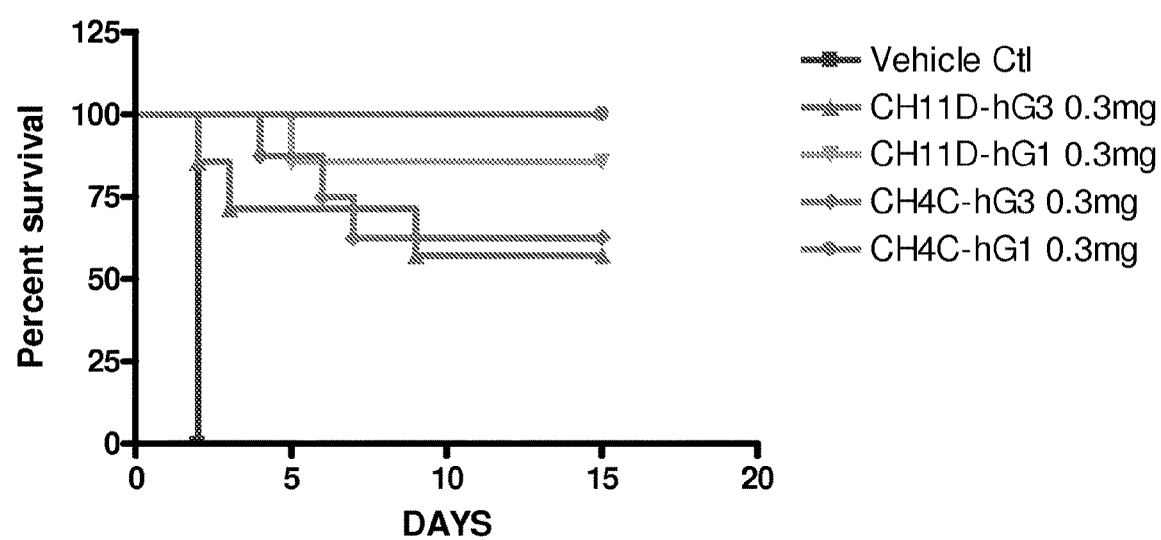
FIG. 5 is a graph showing the effect of IgG1 and IgG3 isotypes of the 4C and 11D monoclonal antibodies on the survival of mice exposed to virulent anthrax spores.

The results showed that all monoclonal antibody-treated groups of mice were completely or partially protected from anthrax infection (Table 3). A comparison of the survival between monoclonal antibody treatments at the lowest dose (0.3 mg/mouse) was statistically evaluated by the Kaplan-Meier and the Logrank (Mantel-Cox) test (GraphPad Prism, Version 4.0, San Diego, Calif.), as shown in FIG. 5. All monoclonal antibody-treated groups at the 0.3 mg/moue dose showed a significant increase in survival when compared to the vehicle-treated group ($p \leq 0.001$). A higher percent survival was also observed with the IgG1 isotype of both the 11D and the 4C monoclonal antibodies when compared to their respective IgG3 isotype monoclonal antibodies at the 0.3 mg/mouse dose, although the difference was not statistically significant by the Logrank test.

infection developed by Lyons et al. (*Infect Immun.* 72(8): 4801-4809, 2004) the efficacy of the monoclonal antibodies 11D and 4C is tested.

Briefly, *B. anthracis* (Ames strain) spore stock is streaked onto a blood agar plate and incubated overnight at 37° C. Prewarmed 2×SG medium is then inoculated with one colony from the overnight plate culture and incubated at 37° C. on a shaker. A sample from this preculture (1.25 ml) is added to 50 ml of 2×SG medium (prewarmed) in a 500-ml filter-top plastic flask and shaken for 24 h. At the end of the 24-hour period, 200 ml of sterile double-distilled $H_2O$ is added to the culture, and incubation is continued with shaking for 40 more hours. After the 40-hour incubation, the sporulation of the culture is evaluated. The culture is then transferred to a sterile centrifuge at 4 to 10° C. for 20 min, washed one time with sterile phosphate-buffered saline (PBS), and resuspended in 50 ml of sterile PBS. The culture is heated to 68° C. for 40 minutes prior to further preparation to remove potentially contaminating vegetative cells. Aliquots of the final solution are transferred into vials and frozen at −80° C. The titer of the stock is determined by plating serial dilutions onto blood agar plates.

An aliquot of the working stock is removed from the freezer and thawed to room temperature in a biohazard hood. The stock is then diluted in serial dilutions with sterile PBS to a desired concentration.

TABLE 3

Survival Following an Intratracheal Challenge with *B. anthracis* (Ames strain) Spores in mAb Pre-Treated BALB/c Mice

| mAb Treatment Group[a] | mAb dose/ mouse | Number of Mice Alive/Day Post-Infection[d] | | | | | | | | | | Percent Survival |
|---|---|---|---|---|---|---|---|---|---|---|---|---|
| | | Day 0[b] | Day 2 | Day 3 | Day 4 | Day 5 | Day 6 | Day 7 | Day 9 | Day 13 | Day 15 | |
| Vehicle Control | None (DPBS)[e] | 8 | 0 | 0 | 0 | 0 | 0 | 0 | 0 | 0 | 0 | 0 |
| CH11D-hG3 | 3 mg | 8 | 8 | 8 | 8 | 8 | 8 | 8 | 7 | 6 | 6 | 75 |
| | 1 mg | 8 | 8 | 8 | 8 | 8 | 8 | 8 | 8 | 8 | 8 | 100 |
| | 0.3 mg | 7[c] | 6 | 5 | 5 | 5 | 5 | 5 | 4 | 4 | 4 | 57 |
| CH11D-hG1 | 3 mg | 7[c] | 7 | 7 | 7 | 7 | 7 | 7 | 7 | 7 | 7 | 100 |
| | 1 mg | 7[c] | 7 | 7 | 7 | 7 | 7 | 7 | 7 | 7 | 7 | 100 |
| | 0.3 mg | 7[c] | 7 | 7 | 7 | 6 | 6 | 6 | 6 | 6 | 6 | 86 |
| CH4C-hG3 | 3 mg | 5[c] | 5 | 4 | 4 | 4 | 4 | 4 | 4 | 4 | 4 | 80 |
| | 1 mg | 7[c] | 7 | 6 | 6 | 5 | 5 | 5 | 5 | 5 | 5 | 71 |
| | 0.3 mg | 8 | 8 | 8 | 7 | 7 | 6 | 5 | 5 | 5 | 5 | 63 |
| CH4C-hG1 | 3 mg | 8 | 8 | 8 | 8 | 8 | 8 | 8 | 8 | 8 | 8 | 100 |
| | 1 mg | 8 | 8 | 8 | 8 | 8 | 8 | 8 | 8 | 8 | 8 | 100 |
| | 0.3 mg | 8 | 8 | 8 | 8 | 8 | 8 | 8 | 8 | 8 | 8 | 100 |

[a]The mice were treated with the designated dose of IgG1 (hG1) or IgG3 (hg3) isotypes of CH11D or CH4C mAbs.
[b]18-24 h post-treatment with mAbs, the mice were infected intratracheally with $1.48 \times 10^4$ *B. anthracis* spores/mouse.
[c]All groups started with 8 mice/group, but a few were lost during the inoculation procedure due to anesthesia complications.
[d]The mice were monitored twice daily. The data indicate the day a change occurred.
[e]1 X Dulbecco's PBS.

The data demonstrate that pre-treatment with the anti-capsular monoclonal antibodies 11D or 4C, at doses as low as 0.3 mg/mouse, provided significant protection against a lethal pulmonary challenge with *B. anthracis* (Ames strain) spores in BALB/c mice and IgG1 was more effective than IgG3 for both monoclonal antibodies.

Example 6

Mouse Model of Anti-γDPGA Protection from Lethal Challenge with *Bacillus anthracis*

This example describes exemplary procedures for testing the efficacy of anti-γDPGA antibodies to treat *Bacillus anthrasis* infections. Using the mouse model of *Bacillus anthrasis*

BALB/c mice between 6 and 8 weeks of age are inoculated and kept in an animal biosafety level 3 containment area. For intranasal (i.n.) inoculations, mice are lightly anesthetized with isoflurane, and a 50-μl inoculum is placed on the nares for inhalation into the lungs. For intra trachea (i.t.) inoculations, mice are anesthetized with avertin and restrained on a small board, a small incision is made through the skin over the trachea, and the underlying tissue is separated. A bent 30-gauge needle attached by sterile polypropylene tubing to a tuberculin syringe is used; the needle is inserted into and parallel with the trachea, and a 50-μl inoculum is delivered into the lung. For subcutaneous (s.c.) inoculation, doses of spores are delivered in a total volume of 200 μl of PBS using a 29-gauge needle attached to an insulin syringe.

Mice are administered a therapeutic amount of anti-γD-PGA antibody. The anti-γDPGA antibody can be administered at doses of 1 µg/kg body weight to about 1 mg/kg body weight per dose, such as 1 µg/kg body weight-100 µg/kg body weight per dose, 100 µg/kg body weight-500 µg/kg body weight per dose, or 500 µg/kg body weight-1000 µg/kg body weight per dose or even greater. The agent can be administered in several doses, for example continuously, daily, weekly, or monthly. In some examples, the mice are administered complement protein or a fragment there of to determine the affects of complement on *B. anthracis* infection via coadministration with the disclosed anti-γDPGA antibodies.

After administration of anti-γDPGA antibody, mice are monitored for signs of disease, for example, from visual inspection and determination of bacterial counts.

Example 7

Treatment of Subjects

This example describes methods that can be used to treat a subject that has or is at risk of having an infection from *B. anthracis*.

In some examples, one or more anti-γDPGA antibodies disclosed herein is administered alone or in combination with one or more isolated anti-anthrax toxin antibodies. or a fragment thereof, such as one or more of an anti-PA, -LF or -EF antibody or a fragment thereof. In particular examples, the method includes screening a subject having, thought to have, or at risk of having (for example due to impaired immunity, physiological status, or exposure to a *B. anthracis*) a *B. anthracis* infection. Subjects of an unknown infection status can be examined to determine if they have an infection, for example using serological tests, physical examination, enzyme-linked immunosorbent assay (ELISA), radiological screening or other diagnostic technique known to those of skill in the art. Subjects found to (or known to) have a *B. anthracis* infection and thereby treatable by administration of one or more of the disclosed anti-γDPGA antibodies are selected to receive anti-γDPGA antibody and optionally one or more isolated anti-anthrax toxin antibodies or fragment thereof, such as one or more of an anti-PA, -LF or -EF antibody or fragment thereof.

Subjects selected for treatment can be administered a therapeutic amount of anti-γDPGA antibody alone or in combination with a therapeutic amount of one or more isolated anti-anthrax toxin antibodies or fragment thereof, such as one or more of an anti-PA, -LF or -EF antibody or fragment thereof. The antibody can be administered at doses of 1 µg/kg body weight to about 1 mg/kg body weight per dose, such as 1 µg/kg body weight-100 µg/kg body weight per dose, 100 µg/kg body weight-500 µg/kg body weight per dose, or 500 µg/kg body weight-1000 µg/kg body weight per dose or even greater. However, the particular dose can be determined by a skilled clinician. The agent can be administered in several doses, for example continuously, daily, weekly, or monthly.

The mode of administration can be any used in the art. The amount of agent administered to the subject can be determined by a clinician, and may depend on the particular subject treated. Specific exemplary amounts are provided herein (but the disclosure is not limited to such doses).

Subjects selected for treatment can also be administered a therapeutic amount of complement protein or a fragment thereof. The complement protein or a fragment thereof can be administered at doses of 1 µg/kg body weight to about 1 mg/kg body weight per dose, such as 1 µg/kg body weight-100 µg/kg body weight per dose, 100 µg/kg body weight-500 µg/kg body weight per dose, or 500 µg/kg body weight-1000 µg/kg body weight per dose. However, the particular dose can be determined by a skilled clinician. The one or more isolated anti-anthrax toxin antibodies or fragment thereof or fragment thereof, such as one or more of an anti-PA, -LF and -EF antibody or fragment thereof, can be administered concurrently or sequentially with the anti-γDPGA antibody. The anti-γDPGA antibody and/or the one or more isolated anti-anthrax toxin antibodies or fragment thereof, such as one or more of an anti-PA, -LF or -EF antibody or fragment thereof, can be administered in one or several doses, for example continuously, daily, weekly, or monthly. When administered sequentially the time separating the administration of the anti-γDPGA antibody and one or more isolated anti-anthrax toxin antibodies or fragment thereof, such as one or more of an anti-PA, -LF or -EF antibody or fragment thereof, can be seconds, minutes, hours, days, or even weeks.

The mode of administration can be any used in the art. The amount of agent administered to the subject can be determined by a clinician, and may depend on the particular subject treated. Specific exemplary amounts are provided herein (but the disclosure is not limited to such doses).

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

We claim:

1. An isolated monoclonal antibody, comprising:
   a heavy chain (H) with a H-complementarity determining region (CDR)1, H-CDR2 and H-CDR3 region and a light chain (L) with a L-CDR1, L-CDR2 and L-CDR3 region, wherein either
   (a) the H-CDR1 comprises the amino acid sequence set forth as amino acids 28 to 32 of SEQ ID NO: 3, the H-CDR2 comprises the amino acid sequence set forth as amino acids 47 to 55 of SEQ ID NO: 3, and the H-CDR3 comprises the amino acid sequence set forth as amino acids 95 to 111 of SEQ ID NO: 3, and wherein the antibody has a light chain with a L-CDR1, L-CDR2 and L-CDR3 region, and wherein L-CDR1 comprises the amino acid sequence set forth as amino acids 23 to 33 of SEQ ID NO: 4, L-CDR2 comprises the amino acid sequence set forth as amino acids 48 to 55 of SEQ ID NO: 4, and L-CDR3 comprises the amino acid sequence set forth as amino acids 88 to 96 of SEQ ID NO: 4; or
   (b) wherein H-CDR1 comprises the amino acid sequence set forth as amino acids 27 to 31 of SEQ ID NO: 5, H-CDR2 comprises the amino acid sequence set forth as amino acids 46 to 54 of SEQ ID NO: 5, and H-CDR3 comprises the amino acid sequence set forth as amino acids 94 to 110 of SEQ ID NO: 5 and wherein the antibody has light chain with a L-CDR1, L-CDR2 and L-CDR3 region, and wherein L-CDR1 comprises the amino acid sequence set forth as amino acids 22 to 32 of SEQ ID NO: 6, L-CDR2 comprises the amino acid sequence set forth as amino acids 47 to 54 of SEQ ID NO: 6, and L-CDR3 comprises the amino acid sequence set forth as amino acids 87 to 95 of SEQ ID NO: 6,
   wherein the antibody specifically binds poly-γ-D-glutamic acid (γDPGA).

2. The isolated monoclonal antibody of claim 1, wherein H-CDR1 comprises the amino acid sequence set forth as amino acids 27 to 31 of SEQ ID NO: 5, H-CDR2 comprises the amino acid sequence set forth as amino acids 46 to 54 of SEQ ID NO: 5, and H-CDR3 comprises the amino acid sequence set forth as amino acids 94 to 110 of SEQ ID NO: 5 and wherein the antibody has light chain with a L-CDR1, L-CDR2 and L-CDR3 region, and wherein L-CDR1 comprises the amino acid sequence set forth as amino acids 22 to 32 of SEQ ID NO: 6, L-CDR2 comprises the amino acid sequence set forth as amino acids 47 to 54 of SEQ ID NO: 6, and L-CDR3 comprises the amino acid sequence set forth as amino acids 87 to 95 of SEQ ID NO: 6.

3. The isolated monoclonal antibody of claim 1, wherein the antibody further comprises a human framework region.

4. The isolated monoclonal antibody of claim 1, wherein the antibody comprises:
   (a) a heavy chain comprising the amino acid sequence according to SEQ ID NO. 3; and
   (b) a light chain comprising the amino acid sequence according to SEQ ID NO. 4.

5. The isolated monoclonal antibody of claim 1, wherein the antibody comprises:
   (a) a heavy chain comprising the amino acid sequence according to SEQ ID NO. 5; and
   (b) a light chain comprising the amino acid sequence according to SEQ ID NO. 6.

6. An isolated functional fragment of the monoclonal antibody of claim 1, wherein the isolated functional fragment specifically binds poly-γ-D-glutamic acid (γDPGA).

7. The isolated functional fragment of the monoclonal antibody of claim 6, wherein the fragment comprises an a Fab' fragment, a F(ab)'₂ fragment, a single chain Fv protein ("scFv"), or a disulfide stabilized Fv protein ("dsFv").

8. The isolated monoclonal antibody of claim 1, wherein the antibody is an IgG.

9. The isolated monoclonal antibody of claim 1, wherein the antibody comprises a human γ1 constant region.

10. The isolated monoclonal antibody of claim 1, wherein the antibody is labeled.

11. The isolated monoclonal antibody of claim 10, wherein the label is a fluorescence, enzymatic, or radioactive label.

12. A nucleic acid molecule encoding the monoclonal antibody of claim 1.

13. The nucleic acid molecule of claim 12, operably linked to a promoter.

14. An expression vector comprising the nucleic acid molecule of claim 13.

15. An isolated host cell transformed with the expression vector of claim 14.

16. The nucleic acid of claim 12, wherein the monoclonal antibody is encoded by the nucleic acid sequence deposited as ATCC Accession No. PTA-9609 or ATCC Accession No. PTA-9610.

17. A hybridoma cell line that produces the monoclonal antibody of claim 1.

18. A pharmaceutical composition comprising the monoclonal antibody of claim 1 and a pharmaceutically acceptable carrier.

19. The pharmaceutical composition of claim 18, further comprising a therapeutically effective amount of one or more isolated anti-anthrax toxin antibodies.

20. The pharmaceutical composition of claim 19, wherein the one or more isolated anti-anthrax toxin antibodies is an anti-protective antigen (PA),-lethal factor (LF)-, or -edema factor (EF) antibody, or an antigen binding fragment thereof.

21. A method for treating or inhibiting a *Bacillus anthracis* infection in a subject, comprising:
    selecting a subject with a *Bacillus anthracis* infection or suspected of having a *Bacillus anthracis* infection; and
    administering to the subject a therapeutically effective amount of the pharmaceutical composition of claim 18, thereby treating the subject.

22. The method of claim 21, further comprising, administering to the subject a therapeutically effective amount of one or more isolated anti-anthrax toxin antibodies or an antigen binding fragment thereof.

23. The method of claim 22, wherein the one or more isolated anti-anthrax toxin antibodies is an anti-protective antigen (PA), -lethal factor (LF), or -edema factor (EF) antibody.

24. A method of detecting *Bacillus anthracis*, comprising:
    contacting a sample suspected of containing *Bacillus anthracis* with the isolated monoclonal antibody of claim 1; and
    detecting binding of the isolated monoclonal antibody to any *Bacillus anthracis* in the sample, wherein detecting binding of the isolated monoclonal antibody to the sample indicates that the sample contains *Bacillus anthracis*.

25. The method of claim 24, wherein the sample is a biological sample obtained from a subject, and the presence of *Bacillus anthracis* in the sample indicates that the subject has a *Bacillus anthracis* infection.

26. The method of claim 24, further comprising
    contacting the sample with a second antibody that specifically binds the isolated monoclonal antibody, and detecting the binding of the second antibody, wherein detecting binding of the binding of the second antibody indicates that the sample contains *Bacillus anthracis*.

27. A method of enhancing opsonophagocytosis of *Bacillus anthracis* in a subject, comprising:
selecting for treatment a subject who is infected by *B. anthracis*; and
administering to the subject an effective amount of the pharmaceutical composition of claim 18,
thereby enhancing the opsonophagocytosis of *Bacillus anthracis* in the subject.

28. A pharmaceutical composition comprising a the antibody of claim 2 and a pharmaceutically acceptable carrier.

29. The pharmaceutical composition of claim 28, further comprising one or more isolated anti-anthrax toxin antibodies or antigen binding fragments thereof, wherein one or more of the anti-anthrax toxin antibodies is an anti-protective antigen (PA) antibody.

* * * * *